US009284305B2

(12) United States Patent
Garner et al.

(10) Patent No.: US 9,284,305 B2
(45) Date of Patent: *Mar. 15, 2016

(54) METHODS OF TREATING OCULAR DISEASES USING DERIVATIVES OF LIPOIC ACID

(71) Applicant: Encore Health, LLC, Roanoke, VA (US)

(72) Inventors: William Garner, Eastport, ME (US); Margaret Garner, Eastport, ME (US); George Minno, Windham, NH (US); David Gooden, Durham, NC (US)

(73) Assignee: Encore Health, LLC, Roanoke, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/303,405

(22) Filed: Jun. 12, 2014

(65) Prior Publication Data

US 2014/0357691 A1 Dec. 4, 2014
US 2015/0246903 A9 Sep. 3, 2015

Related U.S. Application Data

(62) Division of application No. 12/815,586, filed on Jun. 15, 2010, now Pat. No. 8,795,706.

(60) Provisional application No. 61/187,005, filed on Jun. 15, 2009, provisional application No. 61/187,018, filed on Jun. 15, 2009, provisional application No. 61/187,023, filed on Jun. 15, 2009, provisional application No. 61/186,986, filed on Jun. 15, 2009, provisional application No. 61/187,028, filed on Jun. 15, 2009, provisional application No. 61/187,033, filed on Jun. 15, 2009, provisional application No. 61/187,039, filed on Jun. 15, 2009, provisional application No. 61/186,940, filed on Jun. 15, 2009, provisional application No. 61/224,930, filed on Jul. 13, 2009, provisional application No. 61/235,051, filed on Aug. 19, 2009, provisional application No. 61/237,912, filed on Aug. 28, 2009, provisional application No. 61/242,232, filed on Sep. 14, 2009.

(51) Int. Cl.

| A61F 2/02 | (2006.01) |
|---|---|
| C07D 409/12 | (2006.01) |
| A61K 31/765 | (2006.01) |
| A61K 9/00 | (2006.01) |
| A61K 31/095 | (2006.01) |
| A61K 31/381 | (2006.01) |
| A61K 31/382 | (2006.01) |
| A61K 31/385 | (2006.01) |
| A61K 31/4178 | (2006.01) |
| A61K 31/497 | (2006.01) |
| A61K 31/5377 | (2006.01) |
| A61K 31/67 | (2006.01) |
| A61K 31/70 | (2006.01) |
| A61K 31/4025 | (2006.01) |
| A61K 45/06 | (2006.01) |
| C07D 339/04 | (2006.01) |
| A61N 5/06 | (2006.01) |
| A61N 5/067 | (2006.01) |

(52) U.S. Cl.
CPC ............ *C07D 409/12* (2013.01); *A61K 9/0048* (2013.01); *A61K 31/095* (2013.01); *A61K 31/381* (2013.01); *A61K 31/382* (2013.01); *A61K 31/385* (2013.01); *A61K 31/4025* (2013.01); *A61K 31/4178* (2013.01); *A61K 31/497* (2013.01); *A61K 31/5377* (2013.01); *A61K 31/67* (2013.01); *A61K 31/70* (2013.01); *A61K 31/765* (2013.01); *A61K 45/06* (2013.01); *C07D 339/04* (2013.01); *A61N 5/0613* (2013.01); *A61N 2005/067* (2013.01)

(58) Field of Classification Search
CPC .......................... A61K 9/0048; A61K 31/765
See application file for complete search history.

(56) References Cited

U.S. PATENT DOCUMENTS

| 3,238,224 A | 3/1966 | Ohara et al. |
|---|---|---|
| 3,855,240 A | 12/1974 | Mueller |
| 4,210,667 A | 7/1980 | Sarges et al. |
| 4,755,528 A | 7/1988 | DuPriest et al. |
| 5,395,356 A | 3/1995 | King et al. |
| 5,459,133 A | 10/1995 | Neufeld |
| 5,465,737 A | 11/1995 | Schachar |

(Continued)

FOREIGN PATENT DOCUMENTS

| EP | 0 369 880 | 5/1990 |
|---|---|---|
| WO | WO 93/25166 | 12/1993 |

(Continued)

OTHER PUBLICATIONS

Al-Ghoul, K. J., R. K. Nordgren, A. J. Kuszak, C. D. Freel, M. J. Costello, and J. R. Kuszak. 2001. Structural evidence of human nuclear fiber compaction as a function of ageing and cataractogenesis. Experimental eye research 72: 199-214.

Applegate, M. A., K. M. Humphries, and L. I. Szweda. Jan. 2007. Reversible Inhibition of alpha-Ketoglutarate Dehydrogenase by Hydrogen Peroxide: Glutathionylation and Protection of Lipoic Acid. Biochemistry. 47(1): 473-478.

Argirova, M., M. Kleine-Reidick, and W. Breipohl. 2004. Redox status of the eye lens: a regional study. Cell biochemistry and biophysics 41: 381-390.

(Continued)

*Primary Examiner* — Carlos Azpuru
(74) *Attorney, Agent, or Firm* — Sterne, Kessler, Goldstein & Fox P.L.L.C.

(57) ABSTRACT

Dithiol compounds and derivatives thereof are disclosed. The agents are useful for treating an ocular disease, especially presbyopia and cataract. Also provided are methods of treating an ocular disease, the methods comprising administering to a subject an active agent and an adjunctive agent.

35 Claims, 5 Drawing Sheets

(56) References Cited

U.S. PATENT DOCUMENTS

| | | |
|---|---|---|
| 5,466,680 A | 11/1995 | Rudy |
| 5,476,515 A | 12/1995 | Kelman et al. |
| 5,488,050 A | 1/1996 | Neufeld |
| 5,503,165 A | 4/1996 | Schachar |
| 5,527,774 A | 6/1996 | Girard |
| 5,529,076 A | 6/1996 | Schachar |
| 5,624,955 A | 4/1997 | Nagasawa et al. |
| 5,665,770 A | 9/1997 | Terao et al. |
| 5,686,450 A | 11/1997 | Hellberg et al. |
| 5,688,828 A | 11/1997 | Hellberg et al. |
| 5,691,379 A | 11/1997 | Ulrich et al. |
| 5,722,952 A | 3/1998 | Schachar |
| 5,817,630 A | 10/1998 | Hofmann et al. |
| 5,843,184 A | 12/1998 | Cionni |
| 5,869,468 A | 2/1999 | Freeman |
| 5,874,455 A | 2/1999 | Terao et al. |
| 5,888,243 A | 3/1999 | Silverstrini |
| 6,007,510 A | 12/1999 | Nigam |
| 6,013,462 A | 1/2000 | Kauvar et al. |
| 6,030,950 A | 2/2000 | Ohlenschlager |
| 6,063,116 A | 5/2000 | Kelleher |
| 6,153,647 A | 11/2000 | Mallet et al. |
| 6,214,044 B1 | 4/2001 | Silverstrini |
| 6,288,106 B1 | 9/2001 | Pearson et al. |
| 6,313,164 B1 | 11/2001 | Fujita et al. |
| 6,339,102 B1 | 1/2002 | Meyerhoff et al. |
| 6,387,945 B2 | 5/2002 | Packer et al. |
| 6,472,541 B2 | 10/2002 | Tsien et al. |
| 6,664,287 B2 | 12/2003 | Avery et al. |
| 6,703,039 B2 | 3/2004 | Xia et al. |
| 6,743,779 B1 | 6/2004 | Unger et al. |
| 6,923,955 B2 | 8/2005 | Till et al. |
| 7,164,943 B2 | 1/2007 | Roy |
| 7,914,815 B2 | 3/2011 | Till et al. |
| 7,935,332 B2 | 5/2011 | Till |
| 8,147,816 B2 | 4/2012 | Till et al. |
| 8,410,162 B2 | 4/2013 | Garner et al. |
| 8,647,612 B2 | 2/2014 | Garner et al. |
| 8,697,109 B2 | 4/2014 | Garner et al. |
| 8,747,829 B2 | 6/2014 | Till et al. |
| 8,795,706 B2 | 8/2014 | Garner et al. |
| 2002/0025311 A1 | 2/2002 | Till |
| 2002/0035243 A1 | 3/2002 | Imfeld et al. |
| 2003/0187058 A1 | 10/2003 | Hasselwander et al. |
| 2003/0228299 A1 | 12/2003 | Droy-Lefaix et al. |
| 2004/0044227 A1 | 3/2004 | Klatt et al. |
| 2004/0092586 A1 | 5/2004 | Ogata et al. |
| 2005/0101677 A1 | 5/2005 | Till |
| 2005/0112113 A1 | 5/2005 | Till et al. |
| 2005/0130881 A1 | 6/2005 | Shashoura et al. |
| 2005/0137124 A1 | 6/2005 | Castillejos |
| 2005/0171212 A1 | 8/2005 | Gierhart et al. |
| 2005/0287201 A1 | 12/2005 | Till et al. |
| 2006/0177430 A1 | 8/2006 | Bhushan |
| 2006/0188492 A1 | 8/2006 | Richardson et al. |
| 2007/0055070 A1 | 3/2007 | Lawrence |
| 2007/0099845 A1 | 5/2007 | Sheu et al. |
| 2007/0207116 A1 | 9/2007 | Brown |
| 2007/0293562 A1 | 12/2007 | Mylari et al. |
| 2008/0038316 A1 | 2/2008 | Wong et al. |
| 2008/0139990 A1 | 6/2008 | Till et al. |
| 2008/0213239 A1 | 9/2008 | Morris |
| 2009/0082281 A1 | 3/2009 | Shashoua |
| 2009/0093541 A1 | 4/2009 | Ogata |
| 2009/0192212 A1 | 7/2009 | Garner et al. |
| 2009/0227677 A1 | 9/2009 | Garner et al. |
| 2010/0098653 A1 | 4/2010 | Yu et al. |
| 2011/0135622 A1 | 6/2011 | Till et al. |
| 2014/0121266 A1 | 5/2014 | Garner et al. |

FOREIGN PATENT DOCUMENTS

| | | |
|---|---|---|
| WO | WO 93/25199 | 12/1993 |
| WO | WO 94/01773 | 1/1994 |
| WO | WO 02/13863 | 2/2002 |
| WO | WO 02/056804 | 7/2002 |
| WO | WO 03/084532 | 10/2003 |
| WO | WO 2004/028536 | 4/2004 |
| WO | WO 2005/084635 | 9/2005 |
| WO | WO 2006/047080 | 5/2006 |
| WO | WO 2007/011874 | 1/2007 |
| WO | WO 2008/120070 | 10/2008 |
| WO | WO 2010/054135 | 5/2010 |
| WO | WO 2010/147962 | 12/2010 |

OTHER PUBLICATIONS

Ariga T, et al. 2000. Antithrombotic and antineoplastic effects of phyto-organosulfur compounds. Biofactors. 13(1-4):251-5.

Arora A, et al. 2004. Reversal of P-glycoprotein-mediated multidrug resistance by diallyl sulfide in K562 leukemic cells and in mouse liver. Carcinogenesis. 25(6):941-9. Epub Jan. 16, 2004.

Asmellash S, et al. 2005. Modulating the endoplasmic reticulum stress response with trans-4,5-dihydroxy-1,2-dithiane prevents chemically induced renal injury in vivo. Toxicol Sci. 88(2):576-84. Epub Sep. 8, 2005.

Baghieri, S., and M. H. Garner. 1992. Na,K-ATPase and phospholipid degradation in bovine and human lenses. Current eye research 11: 459-467.

Belloir C, et al. 2006. Protective effects of garlic sulfur compounds against DNA damage induced by direct- and indirect-acting genotoxic agents in HepG2 cells. Food Chem Toxicol, 44(6):827-34.

Bilska, A., and L. Wlodek. 2005, Lipoic acid—the drug of the future? Pharmacol Rep 57: 570-577.

Bilska, A., M. Dubiel, M. Sokolowska-Jezewicz, E. Lorenc-Koci, and L. Wlodek. Jun. 2007. Alpha-lipoic acid differently affects the reserpine-induced oxidative stress in the striatum and prefrontal cortex of rat brain. Neuroscience 146: 1758-1771.

Bitar, M. S., S. Wahid, C. W. Pilcher, E. Al-Saleh, and F. Al-Mulla. 2004. Alpha-lipoic acid mitigates insulin resistance in Goto-Kakizaki rats. Hormone and metabolic research. Hormon- und Stoffwechselforschung 36: 542-549.

Blanco, R. A., T. R. Ziegler, B. A. Carlson, P. Y. Cheng, Y. Park, G. A. Cotsonis, C. J. Accardi, and D. P. Jones, Oct. 2007. Diurnal variation in glutathione and cysteine redox states in human plasma. The American journal of clinical nutrition 86: 1016-1023.

Blankenship, T. N., J. F. Hess, and P. G. FitzGerald. 2001. Development- and differentiation-dependent reorganization of intermediate filaments in fiber cells. Investigative ophthalmology & visual science 42: 735-742.

Bonomi, L et al. 1990. Evaluation of the 701 interzeag lens opacity meter. Graefe's Arch Clin Exp Ophthalmol 228(5):447-9.

Borja, D et al. Jun. 2008. Optical Power of the Isolated Human Crystalline Lens. Invest Ophthalmol Vis Sci 49(6):2541-8.

Bron, A.J., et al. "The Ageing Lens" Ophthalmologica (2000) 214(1):86-104.

Brunkener, M., and S. D. Georgatos. 1992. Membrane-binding properties of filensin, a cytoskeletal protein of the lens fiber cells. Journal of cell science 103 ( Pt 3): 709-718.

Cenedella, R. J. 1998. Prenylation of proteins by the intact lens. Investigative ophthalmology & visual science 39: 1276-1280.

Croft, M. A., A. Glasser, G. Heatley, J. McDonald, T. Ebbert, N. V. Nadkarni, and P. L. Kaufman. 2006. The zonula, lens, and circumlental space in the normal iridectomized rhesus monkey eye. Investigative ophthalmology & visual science 47: 1087-1095.

Croft, M. A., and P. L. Kaufman. 2006. Accommodation and presbyopia: the ciliary neuromuscular view. Ophthalmology clinics of North America 19: 13-24, v.

Dubbelman, M., G. L. Van der Heijde, H. A. Weeber, and G. F. Vrensen. 2003. Changes in the internal structure of the human crystalline lens with age and accommodation. Vision research 43: 2363-2375.

Eason, R. C., H. E. Archer, S. Akhtar, and C. J. Bailey. 2002. Lipoic acid increases glucose uptake by skeletal muscles of obese-diabetic ob/ob mice. Diabetes Obes Metab 4: 29-35.

Egan, D., P. James, D. Cooke, and R. O'Kennedy. 1997. Studies on the cytostatic and cytotoxic effects and mode of action of 8-nitro-7-hydroxycoumarin. Cancer letters 118: 201-211.

(56) References Cited

OTHER PUBLICATIONS

Finn, G., B. Creaven, and D. Egan. 2003. Modulation of mitogen-activated protein kinases by 6-nitro-7-hydroxycoumarin mediates apoptosis in renal carcinoma cells. European journal of pharmacology 481: 159-167.

Finn, G. J., B. S. Creaven, and D. A. Egan. 2004. A study of the role of cell cycle events mediating the action of coumarin derivatives in human malignant melanoma cells. Cancer letters 214: 43-54.

Flammer J, Bebie H. 1987. Lens Opacity Meter: a new instrument to quantify lens opacity. Ophthalmologica 195(2):69-72.

Furuta, T., S. S. Wang, J. L. Dantzker, T. M. Dore, W. J. Bybee, E. M. Callaway, W. Denk, and R. Y. Tsien. 1999. Brominated 7-hydroxycoumarin-4-ylmethyls: photolabile protecting groups with biologically useful cross-sections for two photon photolysis. Proceedings of the National Academy of Sciences of the United States of America 96: 1193-1200.

Gail MH & You WC. 2006. A factorial trial including garlic supplements assesses effect in reducing precancerous gastric lesions. J Nutr. 136(3 Suppl):813S-815S.

Garner, M. H., and J. Horwitz. 1994. Catalytic subunit isoforms of mammalian lens Na,K-ATPase. Current eye research 13: 65-77.

Garner, M. H., and Y. Kong. 1999. Lens epithelium and fiber Na,K-ATPases: distribution and localization by immunocytochemistry. Investigative ophthalmology & visual science 40: 2291-2298.

Garner, M. H., and J. R. Kuszak. 1993. Cations, oxidants, light as causative agents in senile cataracts. Puerto Rico health sciences journal 12: 115-122.

Garner, M. H., and A. Spector. 1980. Selective oxidation of cysteine and methionine in normal and senile cataractous lenses. Proceedings of the National Academy of Sciences of the United States of America 77: 1274-1277.

Garner, M. H. 1994. Na,K-ATPases of the lens epithelium and fiber cell: formation of catalytic cycle intermediates and Na+: K+ exchange. Experimental eye research 58: 705-718.

Gilmore WJ & Kirby GM. 2004. Endoplasmic reticulum stress due to altered cellular redox status positively regulates murine hepatic CYP2A5 expression. J Pharmacol Exp Ther. 308(2):600-8. Epub Nov. 10, 2003.

Glasser, A., and M. C. Campbell. 1999. Biometric, optical and physical changes in the isolated human crystalline lens with age in relation to presbyopia. Vision research 39: 1991-2015.

Goulielmos, G., F. Gounari, S. Remington, S. Muller, M. Haner, U. Aebi, and S. D. Georgatos. 1996. Filensin and phakinin form a novel type of beaded intermediate filaments and coassemble de novo in cultured cells. The Journal of cell biology 132: 643-655.

Goulielmos, G., S. Remington, F. Schwesinger, S. D. Georgatos, and F. Gounari. 1996. Contributions of the structural domains of filensin in polymer formation and filament distribution. Journal of cell science 109 ( Pt 2): 447-456.

Green DR & Reed JC. 1998. Mitochondria and apoptosis. Science 281(5381):1309-12.

Gruzman, A., A. Hidmi, J. Katzhendler, A. Haj-Yehie, and S. Sasson. 2004. Synthesis and characterization of new and potent alpha-lipoic acid derivatives. Bioorganic & medicinal chemistry 12: 1183-1190.

Guest, P. C., H. A. Skynner, K. Salim, F. D. Tattersall, M. R. Knowles, and J. R. Atack. 2006. Detection of gender differences in rat lens proteins using 2-D-DIGE. Proteomics 6: 667-676.

Gurney, AM. 1994. Flash photolysis of caged compounds in Microelectrode Techniques, ed Ogden D, pp. 389-406.

Halhal M, et al. 2004. Iontophoresis: from the lab to the bed side. Exp Eye Res 78(3):751-57.

Halleck MM, et al. 1997. Reduction of trans-4,5-dihydroxy-1,2-dithiane by cellular oxidoreductases activates gadd153/chop and grp78 transcription and induces cellular tolerance in kidney epithelial cells. J Biol Chem. 272(35):21760-6.

Hardie, R.C. 1995. Photolysis of Caged Ca2+ Facilitates and inactivates but Does Not Directly Excite Light-Sensitive Channels in Drosophila Photoreceptors. The Journal of Neuroscience 15(1):899-902.

Heidemann, S. R., S. Kaech, R. E. Buxbaum, and A. Matus, 1999. Direct observations of the mechanical behaviors of the cytoskeleton in living fibroblasts. The Journal of cell biology 145: 109-122.

Hermans, E., M. Dubbelman, R. van der Heijde, and R. Heethaar. Jul. 2007. The shape of the human lens nucleus with accommodation. Journal of vision 7: 16.1-10.

Hoenders, H.J., et al. "Lens proteins and aging" J Gerontol (May 1983) 38(3):278-86.

Hofmann, M., P. Mainka, H. Tritschler, J. Fuchs, and G. Zimmer. 1995. Decrease of red cell membrane fluidity and -SH groups due to hyperglycemic conditions is counteracted by alpha-lipoic acid. Archives of biochemistry and biophysics 324: 85-92.

Hung CC, et al. 2003. Protection of renal epithelial cells against oxidative injury by endoplasmic reticulum stress preconditioning is mediated by ERK1/2 activation. J Biol Chem. 278(31):29317-26. Epub May 8, 2003.

Ivanov, D., G. Dvoriantchikova, A. Pestova, L. Nathanson, and V. I. Shestopalov. 2005. Microarray analysis of fiber cell maturation in the lens. FEBS letters 579: 1213-1219.

Janoria, K. G., S. Hariharan, D. Paturi, D. Pal, and A. K. Mitra. 2006. Biotin uptake by rabbit corneal epithelial cells: role of sodium-dependent multivitamin transporter (SMVT). Current eye research 31: 797-809.

Jimenez-Orozco, F. A., J. S. Lopez-Gonzalez, A. Nieto-Rodriguez, M. A. Velasco-Velazquez, J. A. Molina-Guarneros, N. Mendoza-Patino, M. J. Garcia-Mondragon, P. Elizalde-Galvan, F. Leon-Cedeno, and J. J. Mandoki. 2001. Decrease of cyclin D1 in the human lung adenocarcinoma cell line A-427 by 7-hydroxycoumarin. Lung cancer (Amsterdam, Netherlands) 34: 185-194.

Johansson, M., and M. Lundberg. Dec. 2007. Glutathionylation of beta-actin via a cysteinyl sulfenic acid intermediary. BMC Biochem 8: 26.

Jones, D. P., Y. M. Go, C. L. Anderson, T. R. Ziegler, J. M. Kinkade, Jr., and W. G. Kirlin. 2004. Cysteine/cystine couple is a newly recognized node in the circuitry for biologic redox signaling and control. Faseb J 18: 1246-1248.

Jung MY, et al. 2001. Chemopreventive allylthiopyridazine derivatives induce apoptosis in SK-Hep-1 hepatocarcinoma cells through a caspase-3-dependent mechanism. Eur J Cancer. 37(16):2104-10.

Jürgen, W. Mar. 2007. Synthesis and investigations of (6-hydroxy-3-oxo-3H-xanthen-9-yl)methyl derivatives. A new photoremovable protecting group. Inaugural Dissertation at Universität Basel.

Kahn, J., P. Preis, F. Waldman, and A. Tseng, Jr. 1994. Coumarin modulates the cell-cycle progression of an MTV-EJras cell line. Journal of cancer research and clinical oncology 120 Suppl: S19-22.

Kao, J.P.Y. 2006. Caged Molecules: Principles and Practical Considerations. Current Protocols in Neuroscience. 6.20.1-6.20.21.

Kibbelaar, M. A., F. C. Ramaekers, P. J. Ringens, A. M. Selten-Versteegen, L. G. Poels, P. H. Jap, A. L. van Rossum, T. E. Feltkamp, and H. Bloemendal. 1980. Is actin in eye lens a possible factor in visual accomodation? Nature 285: 506-508.

Kim DH, et al. 2005. Aqueous penetration and biological activity of moxifloxacin 0.5% ophthalmic solution and gatifloxacin 0.3% solution in cataract surgery patients. Ophthalmology 112(11):1992-6. Epub Sep. 23, 2005.

Konrad, D., R. Somwar, G. Sweeney, K. Yaworsky, M. Hayashi, T. Ramlal, and A. Klip. 2001. The antihyperglycemic drug alpha-lipoic acid stimulates glucose uptake via both GLUT4 translocation and GLUT4 activation: potential role of p38 mitogen-activated protein kinase in GLUT4 activation. Diabetes 50: 1464-1471.

Krueger, R.R., et al. "Experimental increase in accommodative potential after neodymium: yttrium-aluminum-garnet laser photodisruption of paired cadaver lenses" Ophthalmology (2001) 108(11):2122-29. (Abstract only).

Krumdieck, C.L., et al. "Mechanism of Homocysteine Toxicity on Connective Tissues: Implications for the Morbidity of Aging" J. Nutr. (2000) 130:365S-68S.

Kumar Rv, et al. 1991. The nature of inhibition of 3-hydroxy-3-methylglutaryl CoA reductase by garlic-derived diallyl disulfide. Biochim Biophys Acta. 1078(2):219-25.

Kuszak, J. R., A. R. Khan, and R. J. Cenedella. 1988. An ultrastructural analysis of plasma membrane in the U18666A cataract. Investigative ophthalmology & visual science 29: 261-267.

(56) References Cited

OTHER PUBLICATIONS

Lacy, A., and R. O'Kennedy. 2004. Studies on coumarins and coumarin-related compounds to determine their therapeutic role in the treatment of cancer. Current pharmaceutical design 10: 3797-3811.

Larsson, H. P., A. V. Tzingounis, H. P. Koch, and M. P. Kavanaugh. 2004 Fluorometric measurements of conformational changes in glutamate transporters. Proceedings of the National Academy of Sciences of the United States of America 101: 3951-3956.

Lee V & Bundgaard H. 1992. Improved Ocular Drug Delivery with Prodrugs. In: Sloan K. ed. Produgs: Topical and Ocular Drug Delivery, vol. 53, p. 233.

Lesiński L. & Duschmalé J. 2006. Flash Photolysis in Praktikum "Physikalische Chemie" pp. 1-8.

Li, L., J. Lim, M. D. Jacobs, J. Kistler, and P. J. Donaldson. Mar. 2007. Regional differences in cystine accumulation point to a sutural delivery pathway to the lens core. Invenstigative ophthalmology & visual science 48: 1253-1260.

Lim, J., Y. C. Lam, J. Kistler, and P. J. Donaldson. 2005. Molecular characterization of the cystine/glutamate exchanger and the excitatory amino acid transporters in the rat lens. Investigative ophthalmology & visual science 46: 2869-2877.

Lim, J., L. Li. M. D. Jacobs, J. Kistler, and P. J. Donaldson. Nov. 2007. Mapping of glutathione and its precursor amino acids reveals a role for GLYT2 in glycine uptake in the lens core. Investigative ophthalmology & visual science 48: 5142-5151.

Lindsey Rose, K. M., R. G. Gourdie, A. R. Prescott, R. A. Quinlan, R. K. Crouch. and K. L. Schey. 2006. The C terminus of lens aquaporin 0 interacts with the cytoskeletal proteins filensin and CP49, Investigative ophthalmology & visual science 47: 1562-1570.

Liu H, et al. 1997. Endoplasmic reticulum chaperones GRP78 and calreticulin prevent oxidative stress, Ca2+ disturbances, and cell death in renal epithelial cells. J Biol Chem, 272(35):21751-9.

Liu, J., E. Head, A. M. Gharib, W. Yuan, R. T. Ingersoll, T. M. Hagen, C. W. Cotman, and B. N. Ames. 2002. Memory loss in old rats is associated with brain mitochondrial decay and RNA/DNA oxidation: partial reversal by feeding acetyl-L-carnitine and/or R-alpha -lipoic acid. Proceedings of the National Academy of Sciences of the United States of America 99: 2356-2361.

Lopez-Gonzalez, J. S., H. Prado-Garcia, D. Aguilar-Cazares, J. A. Molina-Guarneros, J. Morales-Fuentes, and J. J. Mandoki. 2004. Apoptosis and cell cycle disturbances induced by coumarin and 7-hydroxycoumarin on human lung carcinoma cell lines. Lung cancer (Amsterdam, Netherlands) 43: 275-283.

Luo, S., V. S. Kansara, X. Zhu, N. K. Mandava, D. Pal, and A. K. Mitra. 2006. Functional characterization of sodium-dependent multivitamin transporter in MDCK-MDR1 cells and its utilization as a target for drug delivery. Mol Pharm 3: 329-339.

Maitra, I., E. Serbinova, H. J. Tritschler, and L. Packer. 1996. Stereospecific effects of R-lipoic acid on buthionine sulfoximine-induced cataract formation in newborn rats. Biochemical and biophysical research communications 221: 422-429.

Maitra, I., E. Serbinova, H. Trischler, and L. Packer. 1995. Alpha-lipoic acid prevents buthionine sulfoximine-induced cataract formation in newborn rats. Free radical biology & medicine 18: 823-829.

Manns, F., J. M. Parel, D. Denham, C. Billotte, N. Ziebarth, D. Borja, V. Fernandez, M. Aly, E. Arrieta, A. Ho, and B. Holden. Jul. 2007. Optomechanical response of human and monkey lenses in a lens stretcher. Investigative ophthalmology & visual science 48: 3260-3268.

Merdes, A., M. Brunkener, H. Horstmann, and S. D. Georgatos. 1991. Filensin: a new vimentin-binding, polymerization-competent, and membrane-associated protein of the lens fiber cell. The Journal of cell biology 115: 397-410.

Merdes, A., F. Gounari, and S. D. Georgatos. 1993. The 47-kD lens-specific protein phakinin is a tailless intermediate filament protein and an assembly partner of filensin. The Journal of cell biology 123: 1507-1516.

Moffat, B.A., et al. "Age-related Changes in the Kinetics of Water Transport in Normal Human Lenses" Exp. Eye Res. (1999) 69(6):663-69.

Moini, H., O. Tirosh, Y. C. Park, K. J. Cho, and L. Packer. 2002. R-alpha-lipoic acid action on cell redox status, the insulin receptor, and glucose uptake in 3T3-L1 adipocytes. Archives of biochemistry and biophysics 397: 384-391.

Muchowski, P. J., M. M. Valdez, and J. I. Clark. 1999. AlphaB-crystallin selectively targets intermediate filament proteins during thermal stress. Investigative ophthalmology & visual science 40: 951-958.

Musk SR, et al. 1997. Cytotoxicity and genotoxicity of diallyl sulfide and diallyl disulfide towards Chinese hamster ovary cells. Food Chem Toxicol. 35(3-4):379-85.

Newell. 1996. Ophthalmology: Principles and Concepts St. Louis: Mosby-Year Book St. Louis, p. 83.

Obrosova I, et al. 1998. Diabetes-induced changes in lens antioxidant status, glucose utilization and energy metabolism: effect of DL-alpha-lipoic acid. Diabetologia 41(12):1442-50.

Ong, M. D., D. M. Payne, and M. H. Garner. 2003. Differential protein expression in lens epithelial whole-mounts and lens epithelial cell cultures. Experimental eye research 77: 35-49.

Pau, H., and J. Kranz. 1991. The increasing sclerosis of the human lens with age and its relevance to accommodation and presbyopia. Graefe's archive for clinical and experimental ophthalmology = Albrecht von Graefes Archly fur klinische and experimentelle Ophthalmologic 229: 294-296.

Petit PX. et al. 1995. Alterations in mitochondrial structure and function are early events of dexamethasone-induced thymocyte apoptosis. J Cell Biol. 130(1):157-67.

Phelps-Brown, N.A., et al. "Nutritional supplements and the eye" Eye (1998) 12:127-33.

Pierscionek, B. K. 1995. Age-related response of human lenses to stretching forces. Experimental eye research 60: 325-332.

Reddy, N. S., K. Gumireddy, M. R. Mallireddigari, S. C. Cosenza, P. Venkatapuram, S. C. Bell, E. P. Reddy, and M. V. Reddy, 2005. Novel coumarin-3-(N-aryl)carboxamides arrest breast cancer cell growth by inhibiting ErbB-2 and ERK1. Bioorganic & medicinal chemistry 13: 3141-3147.

Salvioli S. et al. 1997. JC-1, but not DiOC6(3) or rhodamine 123, is a reliable fluorescent probe to assess delta psi changes in intact cells: implications for studies on mitochondrial functionality during apoptosis. FEBS Lett. 411(1):77-82.

Sandilands, A., A. R. Prescott, A. M. Hutcheson, R. A. Quinlan, J. T. Casselman, and P. G. FitzGerald. 1995. Filensin is proteolytically processed during lens fiber cell differentiation by multiple independent pathways. European journal of cell biology 67: 238-253.

Sarraf D & Lee DA. 1994. The Role of Iontophoresis in Ocular Drug Delivery. J Ocul Pharmacol 10(1):69-81.

Sato. H., M. Tairtba, K. Kuriyama-Matsumura, S. Okuno, and S. Bannai. 2000. Molecular cloning and expression of human xCT, the light chain of amino acid transport system xc. Antioxid Redox Signal 2: 665-671.

Sato, H., M. Tamba, T. Ishii, and S. Bannai. 1999. Cloning and expression of a plasma membrane cystine/glutamate exchange transporter composed of two distinct proteins. The Journal of biological chemistry 274: 11455-11458.

Sato, H., A. Shiiya, M. Kimata, K. Maebara, M. Tamba, Y. Sakakura, N. Makino, F. Sugiyama, K. Yagami, T. Moriguchi, S. Takahashi, and S. Bannai. 2005. Redox imbalance in cystine/glutamate transporter-deficient mice. The Journal of biological chemistry 280: 37423-37429.

Schonheit, K., L. Gille, and H. Nohl. 1995. Effect of alpha-lipoic acid and dihydrolipoic acid on ischemia/reperfusion injury of the heart and heart mitochondria. Biochimica et biophysica acta 1271: 335-342.

Senda, N. 2006. Synthesis and Photochemical Properties of a New Water-Soluble Coumarin, Designed as a Chromophore for Highly Water-Soluble and Photolabile Protecting Group. Bull. Chem. Soc. Jpn. vol. 79, No. 11, 1753-1757.

Shembekar, V. R., Y. Chen, B. K. Carpenter, and G. P. Hess. 2005. A protecting group for carboxylic acids that can be photolyzed by visible light. Biochemistry 44: 7107-7114.

(56) References Cited

OTHER PUBLICATIONS

Spector, A., et al. "Thioredoxin fragment 31-36 is reduced by dihydrolipoamide and reduces oxidized protein" Biochem Biophys Res Commun (Jan. 1988) 150(1):156-62.

Strenk, S. A., L. M. Strenk, J. L. Semmlow, and J. K. DeMarco. 2004. Magnetic resonance imaging study of the effects of age and accommodation on the human lens cross-sectional area. Investigative ophthalmology & visual science 45: 539-545.

Sundaram SG & Milner JA. 1996. Diallyl disulfide suppresses the growth of human colon tumor cell xenografts in athymic nude mice. J Nutr. 126(5):1355-61.

Sweeney, M. H., and R. J. Truscott. 1998. An impediment to glutathione diffusion in older normal human lenses: a possible precondition for nuclear cataract. Experimental eye research 67: 587-595.

Tamm, E., E. Lutjen-Drecoll, W. Jungkunz, and. J. W. Rohen. 1991. Posterior attachment of ciliary muscle in young, accommodating old, presbyopic monkeys. Investigative ophthalmology & visual science 32: 1678-1692.

Tamm, S., E. Tamm, and J. W. Rohen, 1992. Age-related changes of the human ciliary muscle. A quantitative morphometric study. Mechanisms of ageing and development 62: 209-221.

Truscott, R. J. 2000. Age-related nuclear cataract: a lens transport problem. Ophthalmic research 32: 185-194.

Wang, C. J., Y. J. Hsieh, C. Y. Chu, Y. L. Lin, and T. H. Tseng. 2002. Inhibition of cell cycle progression in human leukemia HL-60 cells by esculetin. Cancer letters 183: 163-168.

Wang, S. J., and H. H. Chen. Jan. 2007. Presynaptic mechanisms underlying the alpha-lipoic acid facilitation of glutamate exocytosis in rat cerebral cortex nerve terminals. Neurochemistry international 50: 51-60.

Weeber, HA et al. Feb. 2007. Stiffness gradient in the crystalline lens, Graefes Arch Clin Exp Ophthalmol 245(9):1357-66.

Widomska, J., M. Raguz, J. Dillon, E. R. Gaillard, and W. K. Subczynski. Jun. 2007 Physical properties of the lipid bilayer membrane made of calf lens lipids: EPR spin labeling studies. Biochimica et biophysica acta 1768: 1454-1465.

Wieboldt, R. et al. 1994. Photolabile precursors of glutamate: Synthesis, photochemical properties, and activation of glutamate receptors on a microsecond time scale. Proc. Natl. Acad. Sci, 91:8752-8756.

Willner I & Zahavy E. 1994. Activation of Glutathione Reducase by Light: A Novel Approach to Design Redox Photo-Enzymes. Angew Chem Int Ed Engl 33(5):581-83.

Yin MC, et al. 2002. Nonenzymatic antioxidant activity of four organosulfur compounds derived from garlic. J Agric Food Chem. 50(21):6143-7.

Yu, N. T., D. C. DeNagel, P. L. Pruett, and J. F. Kuck, Jr. 1985. Disulfide bond formation in the eye lens. Proceedings of the National Academy of Sciences of the United States of America 87: 7965-7968.

Zhao, Y., Q. Zheng, K. Dakin, K. Xu, M. L. Martinez, and W. H. Li. 2004. New caged coumarin fluorophores with extraordinary uncaging cross sections suitable for biological imaging applications. Journal of the American Chemical Society 126: 4653-4663.

Zivkovic, D. Apr. 2007. Investigations on 2,7-diamino-9-fluorenol photochemistry. Inaugural Dissertation at Universität Basel.

Ip C, Gunther HE. 1992. Comparison of selenium and sulfur analogs in cancer prevention. Carcinogenesis. 13(7): 1167-70.

Bustamante, J., et al., 1998. α-Lipoic Acid in Liver Metabolism and Disease. Free Radical Biology & Medicine 24: No. 6 1023-1039.

Cagini, C. MD, et al. Apr. 2010. Study of alpha-lipoic acid penetration in the human aqueous humour after topical administration. Clinical and Experimental Ophthalmology "Accepted Article" doi: 10.1111/j. 1442-9071.2010.02319.x.

Giblin FJ, et al. 1979. The effects of X-irradiation on lens reducing systems. Investigative Ophthalmology & Visual Science 18:468-475.

Kramár P, et al. 1987. Thermal cataract formation in rabbits. NCBI Pubmed abstract, PMID: 3426637, abstract of Bioelectromagnetics 8:397-406. (Abstract only).

Li, X., Liu, Z., et al. Apr. 2008. Lipoamide protects retinal pigment epithelial cells from oxidative stress and mitochondrial dysfunction. Free Radic Biol Med. 44(7): 1465-1474.

Lipman RM, et al. 1988. Cataracts induced by Microwave and Ionizing Radiation. NCBI Pubmed abstract, PMID: 3068822, abstract of Surv. Ophthalmol 33:200-210. (Abstract only).

Trayhurn P. and Van Heyningen R. 1973. The Metabolism of Amino Acids in the Bovine Lens; Their Oxidation as a Source of Energy. Biochem. J. 136:67-75.

Wakabayashi, Y. et al. 2006. Glutamate Levels in Aqueous Humor of Patients with Retinal Artery Occlusion. Retina 26:432-436.

Zwingmann, C. et al. 2001. 13C Isotopomer Analysis of Glucose and Alanine Metabolism Reveals Cytosolic Pyruvate Compartmentation as Part of Energy Metabolism in Astrocytes. GLIA 34:200-212.

Aloisi et al. 1948. Glycerylphosphorylcholine and Choline Glycerophosphate. Biochemical Journal. vol. 43, pp. 157-161; p. 157, col. 1, para 2-3; col. 2, para 1; p. 158, col. 1, para 4.

Gilbert, Basic Concepts in Biochemistry USA. McGraw Hill 2000 p. 184.

Jablonski et al. Plant Physiology 1978 61:221-225.

Ng et al. Experimental Eye Research 1986 43:477-489.

Morris Jr. Recent advances in arginine metabolism; roles and regulation of the arginases. British Journal of Pharmacology, E-Pub Jun. 5, 2009, 157(6):922-930.

PubChem Compound Summary CID 863 lipoamide (Sep. 16, 2004) (Retrieved from the internet Nov. 13, 2010; http://pubchem.ncbi.nlm.nih.gov/summary/summary.cgi?cid=863.

Salceda, et al. L-arginine uptake in normal and diabetic rat retina and retinal pigment epithelium. Neurochem Res., Aug. 2008, 33(8):1541-1545.

Stuehr et al. Nw-Hydroxy-L-arginine is an intermediate in the Biosynthesis of nitric Oxide from L-Arginine. The Journal of Biological Chemistry 1991, 266(10):6259-6263.

Truscott. Presbyopia. Emerging from a blur towards an understanding of the molecular basis for this most common eye condition. Exp Eye Res., Epub Jul. 2008, 88(2):241-247; p. 241, col. 1; p. 242, col. 1; p. 245, col. 1.

English Translation of Office Action mailed Jun. 21, 2011, in Japanese Patent Application No. JP 2007-537922 A, filed Dec. 27, 2007.

Extended European Search Report mailed on Apr. 19, 2012, for EP Application No. 09825411.0, European Patent Office, Germany.

Office Action received in U.S. Appl. No. 12/815,586 dated May 9, 2012.

Extended European Search Report mailed on Aug. 21, 2012, for EP Application No. 10790038.3, European Patent Office, Netherlands.

English Translation of Office Action mailed Oct. 12, 2012, in Mexican Patent Application No. MX/a/2007/004775.

Co-pending U.S. Appl. No. 14/170,116, inventors Garner et al., filed Jan. 31, 2014 (Not Published).

Co-pending U.S. Appl. No. 14/275,511, inventors Till et al., filed May 12, 2014 (Not Published).

Glasser, A., "Restoration of accommodation: surgical options for correction of presbyopia," *Clin Exp Optom* 91(3):279-295, Australian Optometrists Association, Australia (May 2008).

McGinty, S. J., and Truscott, R. J. W., "Presbyopia: the first stage of nuclear cataract?" *Opthalmic Res* 38(3):137-148, Karger, Switzerland (Jan. 2006).

Michael, R., and Bron, A. J., "The ageing lens and cataract: a model of normal and pathological ageing," *Phil. Trans. R. Soc. B* 366(1568):1278-1292, The Royal Society, England (Mar. 2011).

Truscott, R J. W., and Zhu, X., "Presbyopia and cataract: a question of heat and time," *Prog Retin Eye Res* 29(6):487-499, Elesevier Ltd., England (Nov. 2010).

Office Action mailed May 5, 2014, in U.S. Appl. No. 13/851,355, inventors Garner et al., filed Mar. 27, 2013.

Office Action mailed Mar. 5, 2014, in U.S. Appl. No. 12/267,208, inventors Garner et al., filed Nov. 7, 2008.

METHODS OF TREATING OCULAR DISEASES USING DERIVATIVES OF LIPOIC ACID

CROSS-REFERENCES TO RELATED APPLICATIONS

This application is a divisional application of U.S. patent application Ser. No. 12/815,586, filed Jun. 15, 2010, now U.S. Pat. No. 8,795,706 B2, which claims the benefit of U.S. Provisional Application Nos. 61/187,005; 61/187,018; 61/187,023; 61/186,986; 61/187.028; 61/187,033; 61/187,039; and 61/186,940; each of which was filed on Jun. 15, 2009, and U.S. Provisional Application Nos. 61/224,930 filed Jul. 13, 2009; 61/235,051 filed Aug. 19, 2009; 61/237,912 filed Aug. 28, 2009; and 61/242,232 filed Sep. 14, 2009.

Each of these applications is incorporated herein by reference in its entirety and for all purposes.

BACKGROUND OF THE INVENTION

As we age, our lenses undergo physiological changes that make it more difficult to focus on near objects. That is why nearly everyone requires reading glasses, even as early as age 35-40. The ability of the eye to change focal power, also known as accommodative amplitude, decreases significantly with age. The accommodative amplitude is 20 diopters in children and young adults, but it decreases to 10 diopters by age 25 and to ≤1 diopter by age 60. The age-related inability to focus on near objects is called presbyopia. All of us will develop presbyopia and will require corrective lenses unless a new treatment is found.

Both presbyopia and cataract are age-related and may share common etiologies such as lens growth, oxidative stress, and/or disulfide bond formation.

There is a need for agents, compositions, and methods for combating ocular disease, including presbyopia and/or cataract.

BRIEF SUMMARY OF THE INVENTION

In one aspect, a compound is provided having the structure of Formula I or pharmaceutically acceptable salt thereof:

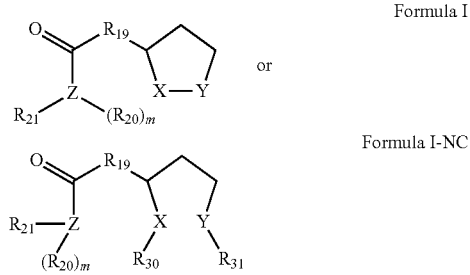

Formula I

Formula I-NC

In Formula I and I-NC, each of X and Y can be sulfur, selenium, or a sulfonic group. In one embodiment, X and Y are both sulfur. In another embodiment, one of X and Y is sulfur, and the other is sulfur or selenium. $R_{19}$ is substituted or unsubstituted alkylene. Each of $R_{20}$, $R_{21}$ $R_{30}$, and $R_{31}$ is independently hydrogen, substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl. Z is N or O. Variable m is 0 or 1, wherein if Z is N, then m is 1, and if Z is O, then m is 0. In one embodiment, $R_{30}$ and $R_{31}$ together form a single bond (thereby creating a structure of Formula I) or are they are substituents joined together to form a heterocyclic ring including X and Y.

In another embodiment, a compound of Formula I, or a pharmaceutically acceptable salt thereof, is employed for pharmaceutical formulations (including a pharmaceutically acceptable excipient) and/or methods of treating ocular disease, e.g., presbyopia or cataract.

DETAILED DESCRIPTION OF THE INVENTION

I. Definitions

Figure 1:
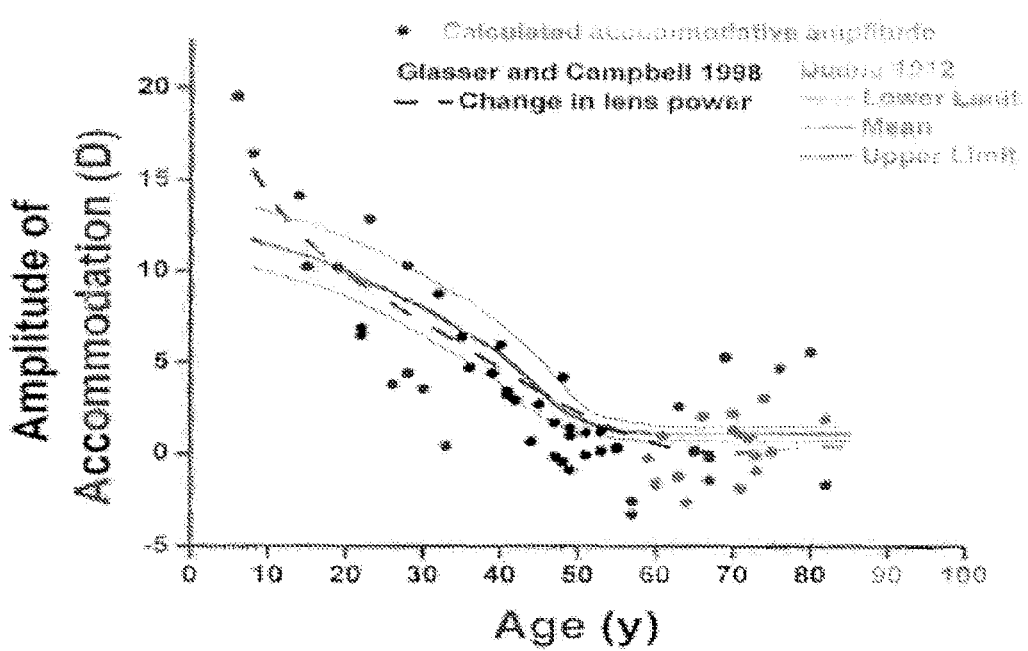
FIG. 1 depicts the accommodative amplitude in diopters (D) of an untreated human lens as a function of age in years. Borja, D et al. 2008. Optical Power of the Isolated Human Crystalline Lens. Invest Ophthalmol Vis Sci 49(6):2541-8. Borja et al. calculated the maximum possible accommodative amplitude of each measured lens power data point (n=65). As shown, there is good agreement between the age-dependent loss of accommodation and the maximum amplitude of accommodation calculated from the isolated lens power.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —$CH_2O$— is equivalent to —$OCH_2$—. In other words, no orientation is implied by the direction that the group is written.

The term "alkyl," by itself or as part of another substituent, means, unless otherwise stated, a straight (i.e., unbranched) or branched chain, or combination thereof, which may be fully saturated, mono- or polyunsaturated (i.e., alkenyl) and can include di- and multivalent radicals (e.g., alkylene), having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups (i.e., alkenyl groups) include, but are not limited to, vinyl, 2-propenyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkthio is an alkyl attached to the remainder of the molecule via a sulfur linker (—S—).

The term "heteroalkyl," by itself or in combination with another term, means, unless otherwise stated, a stable straight or branched chain, or combinations thereof, consisting of at least one carbon atom and at least one heteroatom. A "heteroatom" includes oxygen (O), nitrogen (N), sulfur (S), phosphorus (P), selenium (Se) and silicon (Si), wherein N and S may optionally be oxidized, and N may optionally be quaternized. A heteroatom(s) may be placed at any chemically acceptable position including an interior position, the position at which the alkyl group is attached to the remainder of the molecule (the proximal end), or at the distal end (e.g., for heteroalkylene groups). Examples include, but are not limited to: —C(O)R', —C(O)NR', —NR'R'', —OR', —SR', and/or —$SO_2$R', and —CN. Up to two heteroatoms may be consecutive, such as, for example, —$CH_2$—NH—$OCH_3$.

The terms "cycloalkyl" and "heterocycloalkyl," by themselves or in combination with other terms, mean, unless otherwise stated, cyclic versions of "alkyl" and "heteroalkyl," respectively. Examples of cycloalkyl include, but are not limited to, cyclopropyl, cyclobutyl, cyclopentyl, cyclohexyl, and cycloheptyl. Examples of heterocycloalkyl include, but are not limited to, piperidinyl, piperazinyl, morpholinyl, tetrahydrofuranyl, and tetrahydrothienyl.

The term "aryl" by itself or in combination with another term, means, unless otherwise stated, a polyunsaturated, aromatic, hydrocarbon group, which can be a single ring or multiple rings (preferably from 1 to 3 rings) that are fused together or linked covalently. A fused ring aryl refers to multiple rings fused together wherein at least one of the fused rings is an aryl ring.

The term "heteroaryl" by itself or in combination with another term, means, unless otherwise stated an aryl group (as defined above) containing one to four heteroatoms (as defined above). Thus, the term "heteroaryl" includes fused ring heteroaryl groups, which are multiple rings (e.g., 5 and/or 6-membered rings) fused together wherein at least one of the fused rings is a heteroaromatic ring. A heteroaryl group can be attached to the remainder of the molecule through a carbon or heteroatom. Non-limiting examples of aryl and heteroaryl groups include phenyl, naphthyl, pyrrolyl, pyrazolyl, imidazolyl, pyrazinyl, oxazolyl, thiazolyl, furyl, thienyl, pyridyl, pyrimidyl, purinyl, benzothiazolyl, benzimidazolyl, indolyl, isoquinolyl, quinoxalinyl, 5-quinoxalinyl, and quinolyl.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

For any of the above groups—alkyl, heteroalkyl, cycloalkyl, heterocycloalkyl, aryl, and heteroaryl—the corresponding divalent radical may be referred to with the suffix -ene.

Regarding size, the non-cyclical groups (alkyl and heteroalkyl) typically have 1 to 24 atoms, preferably 1 to 10 atoms, more preferably 1 to 8 atoms (referred to as "lower" substituent group). The cyclical groups (cycloalkyl, heterocycloalkyl, aryl, and heteroaryl) typically have from 3 to 8 members, preferably 4 to 8 members, more preferably 5 to 7 members.

Any of the above groups—alkyl, heteroalkyl, cycloalkyl, heterocycloalkyl, aryl, and heteroaryl—may be unsubstituted or substituted. Exemplary substituents are described below. Further, the substituents themselves may also be unsubstituted or substituted.

A "substituent group," as used herein, means a group selected from the following moieties:

(A) —OH, —$NH_2$, —SH, —CN, —$CF_3$, —$NO_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from: oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

The terms "halo" or "halogen" by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo(C$_1$-C$_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "oxo," as used herein, means an oxygen that is double bonded to a carbon atom.

The term "alkylsulfonyl" means a moiety having the formula —S(O$_2$)—R', where R' is an alkyl group as defined above. R' may have a specified number of carbons (e.g., "C$_1$-C$_4$ alkylsulfonyl").

The substituents can be one ore more one or more of a variety of groups selected from, but not limited to, —OR', —NR'R''', —SR', -halogen, —SiR'R''', R''', —OC(O)R', —C(O)R', —CO$_2$R', —CONR'R''', —OC(O)NR'R''', —NR''C(O)R', —NR'—C(O)NR''R''', —NR''C(O)$_2$R', —NR—C(NR'R''R''')=NR'''', —NR—C(NR'R'')=NR''', —S(O)R', —S(O)$_2$R', —S(O)$_2$NR'R''', —NRSO$_2$R', —CN, and —NO$_2$. Substituents for the non-aromatic groups (alkyl, heteroalkyl, cycloalkyl, and heterocycloalkyl) may also include, e.g., =O, =NR', and =N—OR'. Each of R', R'', R''', and R'''' can be independently hydrogen, substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$).

Substituents for the non-aromatic groups may be present in any number from zero to (2m'+1), where m' is the total number of carbon atoms in the group. Substituents for the aromatic groups (aryl and heteroaryl) may be present in any number from zero to the total number of open valences on the aromatic ring system.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

The symbol "～" denotes the point of attachment of a chemical moiety to the remainder of a molecule or chemical formula.

Certain compounds of the present invention possess asymmetric carbon atoms (optical centers) or double bonds; the racemates, diastereomers, tautomers, geometric isomers, and individual isomers are encompassed within the scope of the present invention. The compounds of the present invention do not include those that are known in the art to be too unstable to synthesize and/or isolate.

The compounds of the present invention may also contain unnatural proportions of atomic isotopes at one or more of the atoms that constitute such compounds. For example, the compounds may be radio-labeled with radioactive isotopes, such as for example tritium ($^3$H), iodine-125 ($^{125}$I), or carbon-14 ($^{14}$C). All isotopic variations of the compounds of the present invention, whether radioactive or not, are encompassed within the scope of the present invention.

Any numerical values recited herein include all values from the lower value to the upper value in increments of any measurable degree of precision. For example, if the value of a variable such as age, amount, time, percent increase/decrease and the like is 1 to 90, specifically from 20 to 80, and more specifically from 30 to 70, it is intended that values such as 15 to 85, 22 to 68, 43 to 51, 30.3 to 32, etc., are expressly enumerated in this specification. In other words, all possible combinations of numerical values between the lowest value and the highest value enumerated are to be considered to be expressly stated in this application in a similar manner.

II. Compounds

There are provided agents, compositions, and methods that can prevent, reduce, reverse, and/or slow the rate of lens growth, oxidative damage, and/or disulfide bond formation. In some embodiments, these agents, compositions, and methods can effectively prevent or treat presbyopia and/or cataract. In one embodiment, the agents, compositions, and methods can effectively prevent or treat presbyopia.

A. Dithiol Compounds and Derivatives

In some embodiments, the agents described herein are dithiol compounds or dithiol derivatives. Dithiol compounds contain at least two sulfur atoms, preferably exactly two sulfur atoms, while dithiol derivatives include a selenium or sulfonic group in place of one or more sulfur atoms of a dithiol compound. Thus, in one embodiment, the agent has at least two components, each independently selected from a sulfur atom, a selenium atom, and a sulfonic group. In another embodiment, the agent has at least two components, each independently selected from a sulfur atom and a selenium atom.

In some embodiments, the agents contemplated herein can be cyclical, e.g., a five- or six-membered heterocycle, or non-cyclical. Exemplary five-membered heterocycles (designated by the term "Formula 5" in the compound name) include, but are not limited to:

Formula 5A

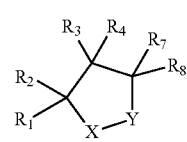

Formula 5B

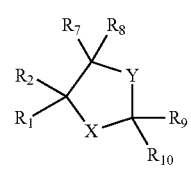

Exemplary six-membered heterocycles (designated by the term "Formula 6" in the compound name) include, but are not limited to:

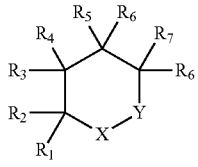

Formula 6A

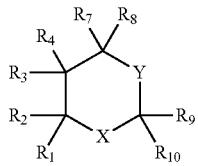

Formula 6B

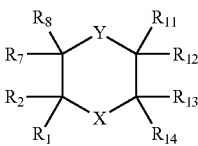

Formula 6C

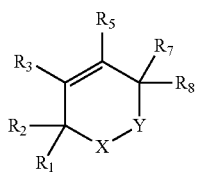

Formula 6D

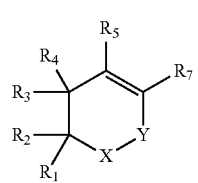

Formula 6E

Exemplary non-cyclical agents (designated by the term "NC" affixed to the formulae designations) include, but are not limited to:

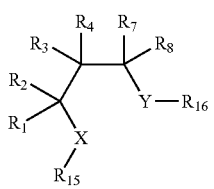

Formula 5-NC

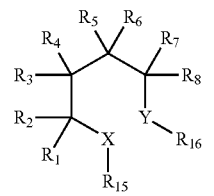

Formula 6-NC

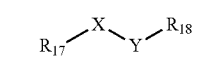

Formula NC

The agents can be classified in various ways. For example, the agent can be encompassed by any one of the following classification groups:

5A, 5B, 6A, 6B, 6C, 6D, and 6E: "cyclical"
5-NC, 6-NC, and NC: "non-cyclical"
5A, 5B, and 5-NC: "5-membered"
5A and 5B: "5-membered cyclical"
6A, 6B, 6C, 6D, 6E, and 6-NC: "6-membered"
6A, 6B, 6C, 6D, and 6E: "6-membered cyclical"
5A and 5-NC: "potential hydrogenation pair"
6A and 6-NC: "potential hydrogenation pair"
5-NC and 6-NC: "potential hydrogenation products"
5A, 6A, 6D, and 6E: "adjacent thiols"
5A and 6A: "adjacent thiols, saturated ring"
6A, 6D, and 6E: "adjacent thiols, 6-membered cyclical"
5B, 6B, and 6C: "non-adjacent thiols"
5B and 6B: "1,3 thiols"
6A, 6B, and 6C: "dithanes"
6D and 6E: "dithiines"
or the agents can be classified by any individual formula.

In some embodiments, substituents X and Y of any of Formulae 5A-B, 6A-E or NC are independently selected from a sulfur atom, a selenium atom, and a sulfonic group. Preferably, at least one of X and Y is sulfur. In one embodiment, X and Y are both sulfur. In another embodiment, one of X and Y is sulfur, and the other is sulfur or selenium. In yet another embodiment, one of X and Y is sulfur, and the other is selenium. In one embodiment, the compound of any of Formulae 5A-B, 6A-E or NC is a seleno derivative where at least one of X and Y is selenium. Without being bound by theory, it is believed that the selenium atom advantageously helps to overcome redox potential.

In some embodiments, each R group of Formulae 5A-B, 6A-E or NC is independently —H, —OH, —OAc, —OR, —SR', —CO$_2$R', an electron withdrawing group, a linear or branched C$_{1-18}$ alkyl optionally substituted by one or more ether, ester, carboxylic acid, phosphate, amide, and/or amine groups, wherein R' is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, each R group is independently —H, —OH, —OAc, —CO$_2$CH$_3$, or a linear C$_{1-18}$ alkyl optionally having a distal terminal that is —COOH, —NH$_2$, —CO$_2$CH$_3$, or —CO$_2$CH$_2$CH$_3$. It is understood that, absent further description, the term "R group" in the context of compounds of any of the formulae described herein refers to any of R$_1$, R$_2$, R$_3$, R$_4$, R$_5$, R$_6$, R$_7$, R$_8$, R$_9$, R$_{10}$, R$_{11}$, R$_{12}$, R$_{13}$, R$_{14}$, R$_{15}$, R$_{16}$, R$_{17}$ or R$_{18}$, R$_{19}$, R$_{20}$, R$_{21}$, R$_{22}$, R$_{23}$, R$_{24}$, R$_{25}$, R$_{26}$, R$_{27}$, R$_{28}$, R$_{29}$, R$_{30}$, R$_{31}$, R$_{32}$, R$_{33}$, and/or R$_{34}$.

In some embodiments, agents can be prepared by altering the placement of a particular R group. For example, any particular R group can be attached to a carbon adjacent to a thiol group (sulfur atom) or thiol derivative (e.g., selenium or sulfonic group). R$_1$, R$_2$, R$_7$, R$_8$, R$_9$, R$_{10}$, R$_{11}$, R$_{12}$, R$_{13}$, and R$_{14}$ represent such thiol-adjacent positions. In other embodiments, an R group can be attached to a carbon not adjacent to a thiol group or thiol derivative. R$_3$, R$_4$, R$_5$, and R$_6$ represent such non-adjacent positions. In yet other embodiments, an R group can be attached directly to a thiol group or thiol derivative. R$_{15}$, R$_{16}$, R$_{17}$, and R$_{18}$ represent such direct thiol or thiol derivative attachments.

In one embodiment, one, two, or more R groups are —H. In some embodiments of Formula 5-NC and 6-NC, both of R$_{15}$ and R$_{16}$ are —H.

In one embodiment, one, two, or more R groups are —OH.

In another embodiment, one, two, or more R groups are —OAc. Without being bound by theory, the addition of an acetate ester (—OAc) is believed to improve corneal permeability, which is especially beneficial for the treatment of presbyopia.

In yet another embodiment, each R group is independently —H, —OH, —OAc, or —CH$_3$.

In another embodiment, one R group is a chain substituent (e.g., substituted or unsubstituted alkyl, preferably a C$_{1-18}$ alkyl), and the remaining R groups are independently —H, —OH, —OAc, or —CH$_3$.

In one embodiment, the agent has the structure of Formula 6A:

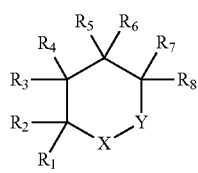

Formula 6A wherein each of R$_1$, R$_2$, R$_7$, and R$_8$ is —H; and R$_3$, R$_4$, R$_5$, and R$_6$ are independently selected from —H, —OH, and —OAc.

In another embodiment, one, two, or more R groups are —CO$_2$R', wherein R' is as defined herein for any of Formulae 5A-B, 6A-E or NC. In another embodiment, one, two, or more R groups are —OR'. In some embodiments, the R' of —CO$_2$R' or —OR' is a lower alkyl group having 1-8 carbons. In one embodiment, —CO$_2$R' is —CO$_2$CH$_3$.

In some embodiments, the agent can be modified by altering the length of the chain substituent(s). Without being bound by theory, longer chains are believed to render the compound more hydrophobic, more lipid soluble, and thus more easily transported across the cell membrane. The length of the chain is limited by the lipid membrane width; a chain longer than the membrane width is likely to cause saponification. Shorter chains, on the other hand, and other similarly small substituents such as —OH and —CO$_2$CH$_3$, may be useful for preparing agents that are biologically active in the cytosol and do not require membrane permeability. Substituent size and its concomitant effect on solubility also affect formulation considerations. For example, a hydrophobic drug may be more difficult to formulate as an administratable solution, but it may be more easily formulated for sustained release delivery systems.

In one embodiment, the agent includes a linear substituted or unsubstituted C$_{1-18}$ alkyl or heteroalkyl, which are collectively referred to herein as "linear substituents." The term "branched substituent" refers to substituted or unsubstituted branched C$_{1-18}$ alkyl or heteroalkyl. Without being bound by theory, linear substituents are more commonly found in natural compounds, so agents including linear substituents may be better tolerated by the body. However, branched substituents may also be used. The linear substituent can be, for example, attached to a carbon adjacent to a thiol group (sulfur atom) or thiol derivative (e.g., selenium or sulfonic group). In some embodiments, one or more of R$_1$, R$_2$, R$_7$, R$_8$, R$_9$, R$_{10}$, R$_{11}$, R$_{12}$, R$_{13}$, and R$_{14}$ is a linear substituent. In other embodiments, one or more of R$_3$, R$_4$, R$_5$, and R$_6$ is a linear substituent.

In one embodiment, a chain substituent (e.g., substituted or unsubstituted alkyl, preferably a C$_{1-18}$ alkyl) includes an ether, ester, carboxylic acid, phosphate, amide, and/or amine group at the distal terminal of a chain. In one embodiment, the distal terminal is a carboxylic acid or an amine. In another embodiment, one, two, or more R groups are —(CH$_2$)$_{2-10}$CO$_2$H or —(CH$_2$)$_{2-10}$NH$_2$. Without being bound by theory, it is believed that carboxylic acid and amine terminals provide attachment points for natural amino acids to form peptide amide bonds. For example, the carboxylic acid terminal of exemplary agent lipoic acid is often covalently attached to the amine lysine side chain of the active mitochondrial enzyme. The mitochondrial functionality of lipoic acid is discussed in further detail below.

In another embodiment, the distal terminal of a chain substituent is an ester, e.g., methyl, ethyl, or isopropyl ester. In one embodiment, one, two, or more R groups are —(CH$_2$)$_{2-10}$CO$_2$CH$_3$ or —(CH$_2$)$_{2-10}$CO$_2$CH$_2$CH$_3$. Without being bound by theory, esterification is believed to be one way to modify the delivery of the pharmaceutical agent since the agent is inhibited from entering the cell until the ester is broken, e.g., by naturally occurring esterases. In this way, an esterified agent can serve as a prodrug that can be converted to an active form, as known in the art.

In one embodiment, the linear substituent is a substituted or unsubstituted linear C$_{1-18}$, C$_{2-12}$, C$_{2-10}$, C$_{2-8}$, C$_{2-6}$, C$_{4-6}$, C$_{5-6}$, or C$_5$ alkyl. Exemplary agents including a linear alkyl substituent are provided in Table 1 following, wherein the remaining R groups which are not expressly defined in Table 1 are independently —H, —OH, —OAc, or —CH$_3$.

TABLE 1

| Formula | X, Y | R |
|---|---|---|
| 5A; 5-NC; or 6B | X is S and Y is S | R$_1$ or R$_3$ is:<br>—(CH$_2$)$_{3-10}$CO$_2$H;<br>—(CH$_2$)$_{3-10}$CO$_2$CH$_3$; or<br>—(CH$_2$)$_{3-10}$CO$_2$CH$_2$CH$_3$ |
| 5A; 5-NC; or 6B | X is S and Y is S;<br>X is S and Y is Se; or<br>X is Se and Y is S | R$_1$ or R$_3$ is:<br>—(CH$_2$)$_{1-2}$CO$_2$H;<br>—(CH$_2$)$_{1-2}$CO$_2$CH$_3$;<br>—(CH$_2$)$_{1-2}$CO$_2$CH$_2$CH$_3$; or<br>—(CH$_2$)$_{2-10}$NH$_2$ |
| 5A 5-NC 6B | X is S and Y is Se; or<br>X is Se and Y is S | R$_1$ or R$_3$ is:<br>—(CH$_2$)$_{3-10}$CO$_2$H;<br>—(CH$_2$)$_{3-10}$CO$_2$CH$_3$; or<br>—(CH$_2$)$_{3-10}$CO$_2$CH$_2$CH$_3$ |
| 6A 6-NC | X is S and Y is S;<br>X is S and Y is Se; or<br>X is Se and Y is S | R$_1$ or R$_3$ is:<br>—(CH$_2$)$_{2-10}$CO$_2$H;<br>—(CH$_2$)$_{2-10}$NH$_2$;<br>—(CH$_2$)$_{2-10}$CO$_2$CH$_3$; or<br>—(CH$_2$)$_{2-10}$CO$_2$CH$_2$CH$_3$ |
| 5B | X is S and Y is S;<br>X is S and Y is Se; or<br>X is Se and Y is S | R$_1$ or R$_9$ is:<br>—(CH$_2$)$_{2-10}$CO$_2$H;<br>—(CH$_2$)$_{2-10}$NH$_2$;<br>—(CH$_2$)$_{2-10}$CO$_2$CH$_3$; or<br>—(CH$_2$)$_{2-10}$CO$_2$CH$_2$CH$_3$ |
| 6D 6E | X is S and Y is S;<br>X is S and Y is Se; or<br>X is Se and Y is S | R$_1$, R$_3$, R$_5$, or R$_7$ is:<br>—(CH$_2$)$_{2-10}$CO$_2$H;<br>—(CH$_2$)$_{2-10}$NH$_2$;<br>—(CH$_2$)$_{2-10}$CO$_2$CH$_3$; or<br>—(CH$_2$)$_{2-10}$CO$_2$CH$_2$CH$_3$ |

Exemplary agent lipoic acid and some derivatives thereof include a divalent linear alkylene functionality with a carboxylic acid terminal:

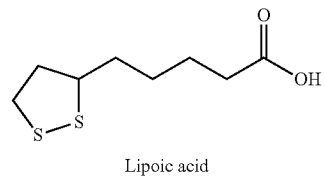

Lipoic acid

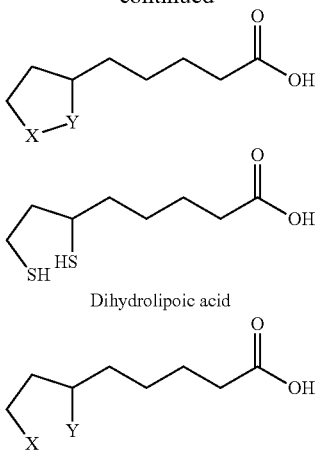

Dihydrolipoic acid

In one embodiment, the agent is lipoic acid (5-(1,2-dithiolan-3-yl)pentanoic acid), particularly alpha lipoic acid. In another embodiment, the agent is a lipoic acid derivative. Preferred lipoic acid derivatives do not interfere with the natural cellular mechanisms utilizing lipoic acid and/or dihydrolipoic acid. The agents described herein include those having relatively minor modifications to lipoic acid (e.g., altering chain length, replacing a sulfur atom with selenium) such that naturally occurring mitochondrial mechanisms can utilize either lipoic acid or the derivative. Agents having minor modifications may be relatively substitutable for lipoic acid and do not interfere with mitochondrial activity. Thus, in one embodiment, the agent functionally mimics lipoic acid in terms of redox activity and/or mitochondrial activity, but is not structurally identical to lipoic acid. Other agents include those having more major modifications to lipoic acid (e.g., altering chain placement). Such major modifications may render the agent unrecognizable to the mitochondria, thus avoiding interference with cellular mechanisms. In this way, both minor and major modifications can avoid mitochondrial interference. Mitochondrial interference, or the lack thereof, can be verified by in vitro testing according to methods known in the art such as, for example, a JC-1 Mitochondrial Membrane Potential Assay Kit (Cell Tech. Inc.). One of ordinary skill in the art could balance the strength of the reducing agent, which is believed to be responsible for the therapeutic effect, against mitochondrial interference, which might cause adverse effects. Exemplary lipoic acid derivatives include, but are not limited to: 5-(1,2-thiaselenolan-5-yl)pentanoic acid and 5-(1,2-thiaselenolan-3-yl)pentanoic acid.

Without being bound by theory, it is believed that lipoic acid or derivatives thereof, may upregulate antioxidant pathways (e.g., thioredoxin). Key to this upregulation is the Nrf2 response element. See Li, X., Liu, Z., et al. 2008. Lipoamide protects retinal pigment epithelial cells from oxidative stress and mitochondrial dysfunction. Free Radic Biol Med. 44(7): 1465-1474. This suggests that the mechanism of action for lipoic acid and derivatives includes not only its antioxidant properties, but also an upregulation of other enzymes.

In another embodiment, the linear substituent is a linear $C_{1-18}$, $C_{1-8}$, $C_{5-15}$, $C_{10-18}$, or $C_{10-16}$, or $C_{12-14}$ alkenyl, the alkenyl chain of which can have one, two, three, or more double bonds. Without being bound by theory, linear alkenyls of relatively longer length, e.g., $C_{10-18}$, particularly those including a carboxylic acid or ester group, may exhibit advantageous properties similar to a fatty acid group.

Alkenyls, including those of shorter lengths, are also useful, especially for embodiments of Formula NC. For example, in one embodiment, each of $R_{17}$ and $R_{18}$ is independently selected from $C_{2-8}$, $C_{2-6}$, $C_{3-6}$, $C_{3-5}$, or $C_3$ alkenyl. In another embodiment of Formula NC., $R_{17}$ and/or $R_{18}$ is an —$SC_{2-8}$ alkenyl.

A chain substituent can include more than one substituent. For example, one exemplary agent is cystine (3,3'-disulanedylbis(2-aminopropanoic acid)), which includes both carboxylic acid and amine substituents. In one embodiment, the agent is cystine or a derivative thereof such as the exemplary derivative shown below:

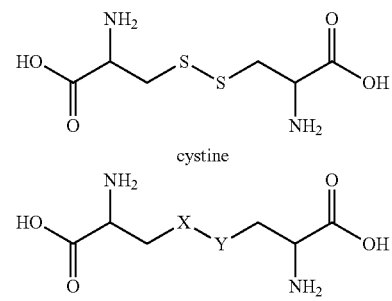

cystine

In another embodiment, an R group substituent is an electron withdrawing group, which can decrease the pKa of the agent. Electron withdrawing groups include, but are not limited to halogens (e.g., F, Cl), nitriles (CN), carboxylic acids (COOH), and carbonyls (CO).

In one embodiment, the agent is an allium oil antioxidant or a derivative thereof. Allium oil antioxidants are advantageously natural, nontoxic, and lipid soluble. Some have been studied as potential cytostatic agents for the treatment of atherlerosclerosis, cancer, etc. Without being bound be theory, the cytostatic properties may also provide advantageous efficacy in the context of ocular diseases caused by lens growth, including presbyopia and cataract.

One class of allium oil antioxidants is the dithiines. Exemplary dithiines include, but are not limited to:

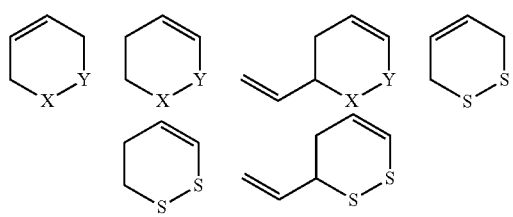

3,6-dihydro-1,2-dithiine    3,4-dihydro-1,2-dithiine    3-vinyl-[4H]-1,2-dithiine Other allium oil antioxidants include, but are not limited to:

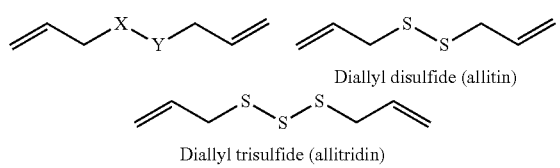

Diallyl disulfide (allitin)

Diallyl trisulfide (allitridin)

-continued

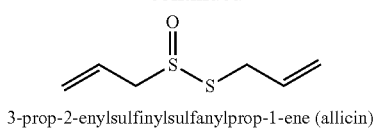

3-prop-2-enylsulfinylsulfanylprop-1-ene (allicin)

In another embodiment, the agent can be a dithiane or a derivative thereof. Without being bound by theory, it is believed that dithianes increase cellular non-protein SH, a primary objective in the treatment of presbyopia. Exemplary dithianes include, but are not limited to:

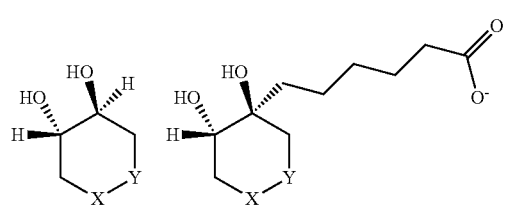

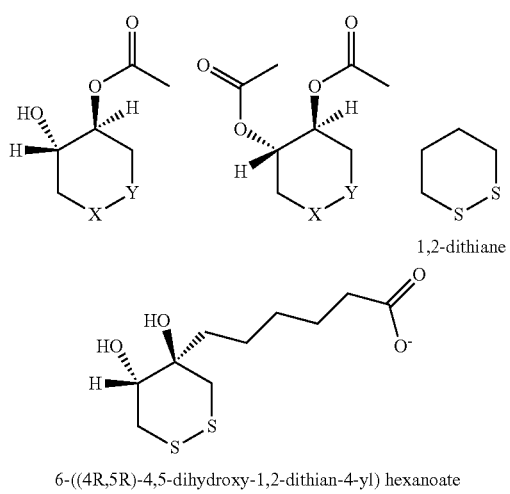

6-((4R,5R)-4,5-dihydroxy-1,2-dithian-4-yl) hexanoate

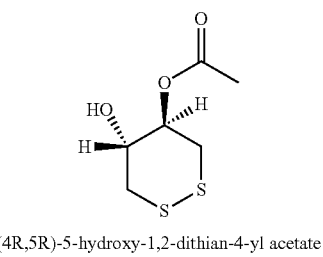

(4R,5R)-5-hydroxy-1,2-dithian-4-yl acetate

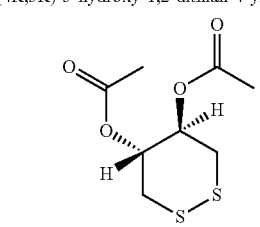

(4R,5R)-1,2-dithian-4,5-diyl diacetate

In one embodiment, the agent is a derivative of dithiothreitol (DTT) such as trans-4,5-dihydroxy-1,2-dithiane, also referred to herein as "non-lethal DTT":

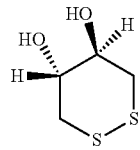

Trans-4,5-dihydroxy-1,2-dithiane (Non-lethal DTT)

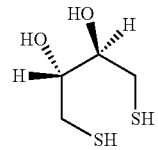

Dithiothreitol (DTT)

Both DTT and non-lethal DTT possess potent antioxidant properties, but non-lethal DTT possesses the further advantage of reduced toxicity thereby being more favorable for use in in vivo settings.

B. Amides and Esters

In certain embodiments, the compound is a heterocyclic ester or amide having the structure of Formula I:

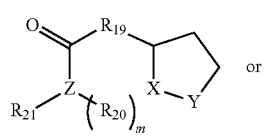

Formula I or

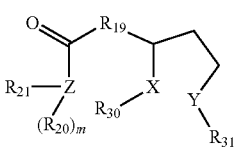

Formula I-NC wherein X and Y are as defined above, and Z is nitrogen (N) or oxygen (O), and m is 0 or 1, wherein if Z is N, then m is 1, and if Z is O, then m is 0.

$R_{19}$ is $R_{22}$-substituted or unsubstituted alkylene, or $R_{22}$-substituted or unsubstituted heteroalkylene, wherein $R_{22}$ is independently substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl. In one embodiment, $R_{19}$ is a substituted or unsubstituted alkylene, e.g., a $C_{1-8}$, $C_{1-6}$, $C_{3-5}$, or $C_4$ alkylene.

$R_{20}$ is hydrogen, $R_{23}$-substituted or unsubstituted alkyl, $R_{23}$-substituted or unsubstituted cycloalkyl, $R_{23}$-substituted or unsubstituted heteroalkyl, $R_{23}$-substituted or unsubstituted heterocycloalkyl, $R_{23}$-substituted or unsubstituted aryl, or $R_{23}$-substituted or unsubstituted heteroaryl. $R_{23}$ is independently —$NH_2$, =NH, —$PO_3H_2$, —OH, —$CO_2H$, $R_{24}$-substituted or unsubstituted alkyl, $R_{24}$-substituted or unsubstituted cycloalkyl, $R_{24}$-substituted or unsubstituted heteroalkyl, $R_{24}$-substituted or unsubstituted heterocycloalkyl, $R_{24}$-substituted or unsubstituted aryl, or $R_{24}$-substituted or unsubstituted heteroaryl. $R_{24}$ is independently —$NH_2$, =NH, —$PO_3H_2$, —OH, —$CO_2H$, $R_{25}$-substituted or unsubstituted alkyl, $R_{25}$-substituted or unsubstituted cycloalkyl, $R_{25}$-substituted or unsubstituted heteroalkyl, $R_{25}$-substituted or unsubstituted heterocycloalkyl, $R_{25}$-substituted or unsubstituted aryl, or $R_{25}$-substituted or unsubstituted heteroaryl. $R_{25}$ is independently unsubstituted alkyl, unsubstituted cycloalkyl, unsubstituted heteroalkyl, unsubstituted heterocycloalkyl, unsubstituted aryl or unsubstituted heteroaryl. In some embodiments, $R_{20}$ is hydrogen or an unsubstituted lower alkyl, e.g., methyl, ethyl, propyl, or butyl. In another embodiment, $R_{20}$ is hydrogen.

$R_{21}$ is $R_{26}$-substituted or unsubstituted alkyl, $R_{26}$-substituted or unsubstituted cycloalkyl, $R_{26}$-substituted or unsubstituted heteroalkyl, $R_{26}$-substituted or unsubstituted heterocycloalkyl, $R_{26}$-substituted or unsubstituted aryl, or $R_{26}$-substituted or unsubstituted heteroaryl. $R_{26}$ is independently —$NH_2$, =NH, —$PO_3H_2$, —OH, —$CO_2H$, $R_{27}$-substituted or unsubstituted alkyl, $R_{27}$-substituted or unsubstituted cycloalkyl, $R_{27}$-substituted or unsubstituted heteroalkyl, $R_{27}$-substituted or unsubstituted heterocycloalkyl, $R_{27}$-substituted or unsubstituted aryl, or $R_{27}$-substituted or unsubstituted heteroaryl. $R_{27}$ is independently —$NH_2$, =NH, —$PO_3H_2$, —OH, —$CO_2H$, $R_{28}$-substituted or unsubstituted alkyl, $R_{28}$-substituted or unsubstituted cycloalkyl, $R_{28}$-substituted or unsubstituted heteroalkyl, $R_{28}$-substituted or unsubstituted heterocycloalkyl, $R_{28}$-substituted or unsubstituted aryl, or $R_{28}$-substituted or unsubstituted heteroaryl. $R_{28}$ is independently unsubstituted alkyl, unsubstituted cycloalkyl, unsubstituted heteroalkyl, unsubstituted heterocycloalkyl, unsubstituted aryl or unsubstituted heteroaryl.

$R_{30}$ and $R_{31}$ are each independently selected from hydrogen, $R_{32}$-substituted or unsubstituted alkyl, $R_{32}$-substituted or unsubstituted cycloalkyl, $R_{32}$-substituted or unsubstituted heteroalkyl, $R_{32}$-substituted or unsubstituted heterocycloalkyl, $R_{32}$-substituted or unsubstituted aryl, or $R_{32}$-substituted or unsubstituted heteroaryl. $R_{32}$ is independently —$NH_2$, =NH, —$PO_3H_2$, —OH, —$CO_2H$, $R_{33}$-substituted or unsubstituted alkyl, $R_{33}$-substituted or unsubstituted cycloalkyl, $R_{33}$-substituted or unsubstituted heteroalkyl, $R_{33}$-substituted or unsubstituted heterocycloalkyl, $R_{33}$-substituted or unsubstituted aryl, or $R_{33}$-substituted or unsubstituted heteroaryl. $R_{33}$ is independently —$NH_2$, =NH, —$PO_3H_2$, —OH, —$CO_2H$, $R_{34}$-substituted or unsubstituted alkyl, $R_{34}$-substituted or unsubstituted cycloalkyl, $R_{34}$-substituted or unsubstituted heteroalkyl, $R_{34}$-substituted or unsubstituted heterocycloalkyl, $R_{34}$-substituted or unsubstituted aryl, or $R_{34}$-substituted or unsubstituted heteroaryl. $R_{34}$ is independently unsubstituted alkyl, unsubstituted cycloalkyl, unsubstituted heteroalkyl, unsubstituted heterocycloalkyl, unsubstituted aryl or unsubstituted heteroaryl. In some embodiments, $R_{30}$ and $R_{31}$ are each independently hydrogen or an unsubstituted lower alkyl. In another embodiment, $R_{30}$ and $R_{31}$ are each hydrogen.

In some embodiments, $R_{30}$ and $R_{31}$ together form a single bond (thereby creating a structure of Formula I) or are they are substituents (e.g., substituted or unsubstituted alkyl or substituted or unsubstituted heteroalkyl) joined together to form a heterocyclic ring including X and Y.

It is understood that each substituent on an alkyl, cycloalkyl, heteroalkyl, heterocycloalkyl, aryl or heteroaryl may occur multiple times, each occurrence being independently chosen.

It is understood that the position in the heterocycle of Formula I which is vicinal to X can be an asymmetric center. Accordingly, the (R) and (S) enantiomers of Formula I are contemplated for compounds of described herein, as shown following.

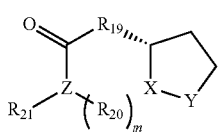

Formula I(R)

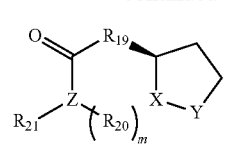

Formula I(S)

Any of the Formulae herein may be similarly designated R and S. Unless specifically indicated to the contrary, the compounds contemplated herein include all optical isomers, regioisomers, enantiomers and/or diastereomers thereof. In one embodiment, the compound is the R enantiomer.

In some embodiments, the compound has the structure of Formula I, provided however that the compound is not lipoic acid.

1. Amides

In some embodiments, the compound is an optionally substituted heterocyclic amide having the structure of Formula II:

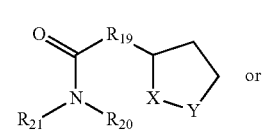

Formula II or

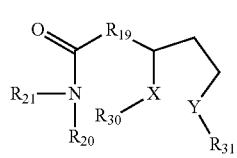

Formula II-NC wherein $R_{19}$, $R_{20}$, $R_{21}$, $R_{30}$, $R_{31}$, X and Y are as defined above.

In some embodiments, the compound of Formula II has the structure of Formula III:

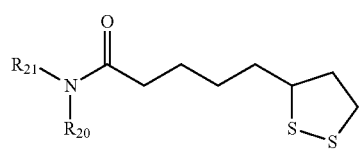

Formula III where $R_{20}$ and $R_{21}$ are as defined above.

In some embodiments, $R_{21}$ is $R_{26}$-substituted alkyl or $R_{26}$-substituted heteroalkyl, wherein $R_{26}$ is present in one or more occurrences, and in each occurrence is independently amine, —$NH_2$, =NH, —$PO_3H_2$, —OH, —$CO_2H$, $R_{27}$-substituted or unsubstituted alkyl, $R_{27}$-substituted or unsubstituted cycloalkyl, $R_{27}$-substituted or unsubstituted heteroalkyl, $R_{27}$-substituted or unsubstituted heterocycloalkyl, $R_{27}$-substituted or unsubstituted aryl, or $R_{27}$-substituted or unsubstituted heteroaryl. In some embodiments, $R_{21}$ is aminoalkyl, preferably aminoethyl. In some embodiments, $R_{21}$ is N-substituted aminoalkyl, preferably N-substituted aminoethyl, wherein the pendant amino functionality is in turn substituted with $R_{27}$ (e.g., (N,N-dialkylamino)-alkyl, preferably dimethylaminoethyl). In some embodiments, $R_{27}$ is $C_1$-$C_6$ alkyl, preferably methyl. In some embodiments, $R_{21}$ is phosphonoylalkyl, preferably phosphonoylethyl. In some embodiments, $R_{21}$ is hydroxyalkyl, preferably hydroxyethyl. In some embodiments, $R_{21}$ is hydroxyalkyl, preferably hydroxyethyl, and $R_{20}$ is unsubstituted alkyl, preferably $C_1$-$C_6$ alkyl, more preferably methyl. In some embodiments, $R_{21}$ is hydroxyethyl, and $R_{20}$ is methyl. In some embodiments, $R_{21}$ is alkyl which in turn is multiply substituted with —OH (e.g., 2,3-dihydroxypropyl), and $R_{20}$ is hydrogen.

In some embodiments, $R_{21}$ is $R_{26}$-substituted or unsubstituted heterocycloalkyl. Exemplary heterocycloalkyl functionalities include, but are not limited to, morpholino and piperazinyl. In some embodiments, $R_{21}$ is $R_{26}$-substituted tetrahydropyranyl, preferably 3,4,5,6-tetrahydroxytetrahydro-2H-pyran-2-yl). In some embodiments, $R_{26}$ is multiply substituted with hydroxyl. In some embodiments, $R_{21}$ is $R_{26}$-substituted morpholino, wherein $R_{26}$ is $C_1$-$C_6$ alkyl, preferably methyl.

In some embodiments, $R_{21}$ is $R_{26}$-substituted or unsubstituted heteroaryl, preferably (1H-imidazol-2-yl)ethyl.

In some embodiments, $R_{21}$ is $R_{26}$-substituted heteroalkyl, wherein the $R_{26}$-substituted heteroalkyl includes a repeating polymeric unit. Exemplary polymeric units in this context include, but are not limited to, polyethylene glycol [(—$CH_2$—$CH_2$—O—)$_n$, wherein n>1], as known in the art.

In some embodiments, $R_{21}$ is as defined above, and $R_{20}$ is $C_1$-$C_6$ alkyl, preferably methyl, ethyl or isopropyl, more preferably methyl.

In some embodiments, $R_{21}$ is $R_{26}$-substituted alkyl or $R_{26}$-substituted heteroalkyl, wherein $R_{26}$ is present in one or more occurrences, and in each occurrence is independently unsubstituted alkyl. In some embodiments, $R_{21}$ is aminoalkyl, preferably aminoethyl, and $R_{26}$ is independently present at the pendant nitrogen 0, 1, 2 or even 3 times.

In some embodiments, $R_{20}$ and $R_{21}$ are independently hydrogen.

In some embodiments, the compound of Formula III includes an amino acid bound in amide linkage between an alpha nitrogen of the amino acid or a side chain nitrogen of the amino acid, and the acid functionality of lipoic acid, having the structure of either of Formula IVA-IVB following.

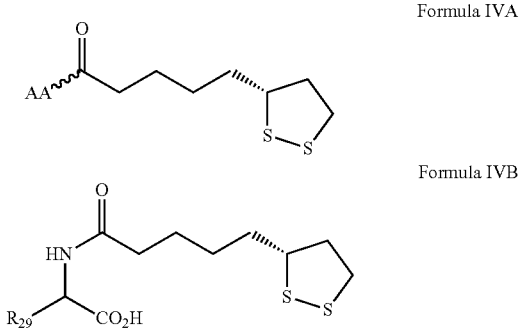

Formula IVA

Formula IVB

Regarding Formulae IVA-B, the term "AA" refers to an amino acid having a side chain nitrogen in amide linkage with the lipoic acid functionality, and $R_{29}$ is the side chain of an alpha amino acid, preferably a naturally occurring amino acid or homolog thereof. The linkage between the side chain nitrogen of the amino acid "AA" is indicated by the symbol "∿" in Formulae IVA. Exemplary amino acids include, but are not limited to, the naturally occurring amino acids and homologs thereof (e.g., diaminoproprionic acid, diaminobutyric acid, ornithine, lysine, homolysine), as known in the art. Both D/L (R/S) stereoisomers of the amino acids are contemplated herein. Further exemplary amino acid amides of lipoic acid having the structure of Formulae IVA-IVB include, but are not limited to, the compounds set forth below:

TABLE 2

Amino acid amides

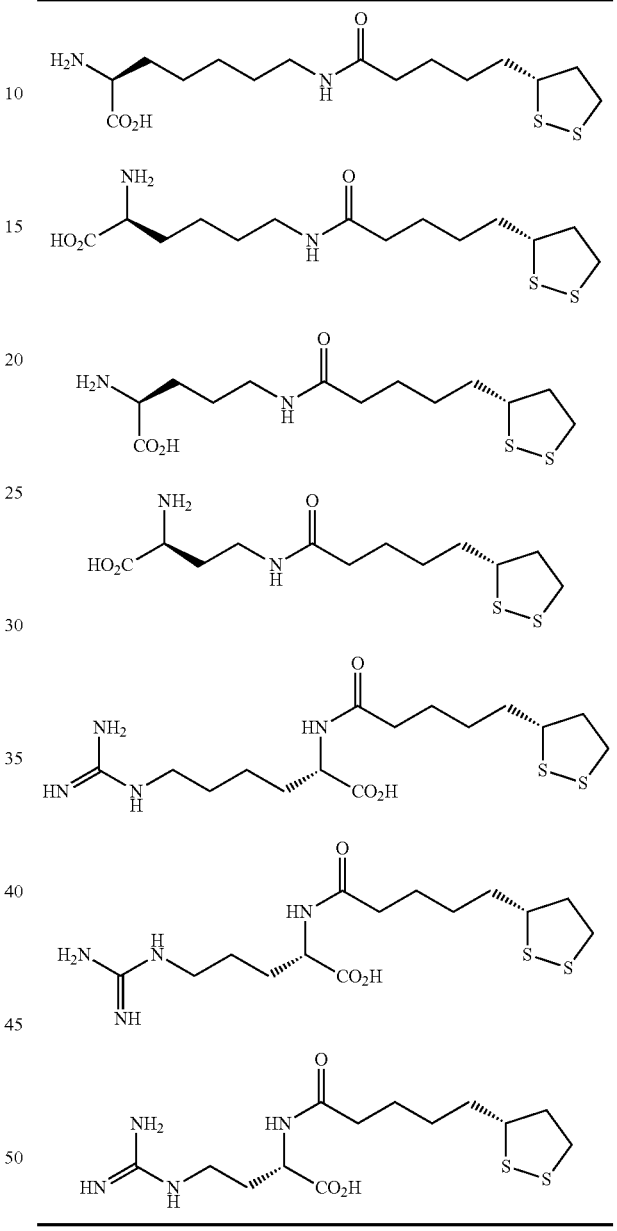

In some embodiments, a compound is provided as set forth below:

TABLE 3

Active agent amides

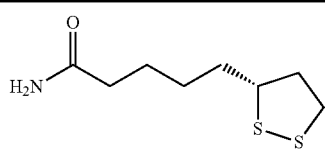

TABLE 3-continued

Active agent amides

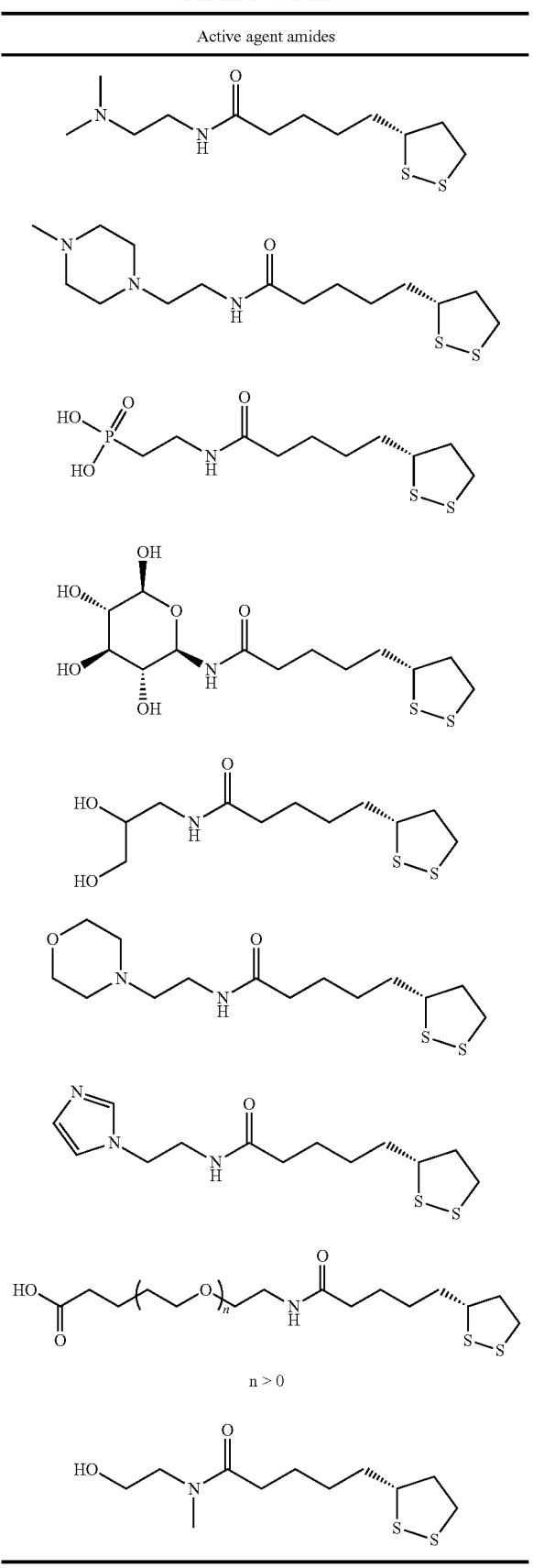

2. Esters

In some embodiments, there is provided an optionally substituted heterocyclic-containing ester of Formula I having the structure of Formula V:

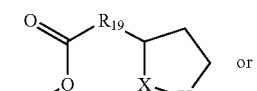
Formula V

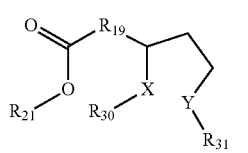
Formula V-NC wherein $R_{19}$, $R_{21}$, $R_{30}$, $R_{31}$, X, and Y are as defined above.

In some embodiments of the compound of Formula V or V-NC, $R_{19}$ is unsubstituted alkylene, preferably $C_1$-$C_6$ alkylene, more preferably $C_4$ alkylene. In some embodiments, $R_{19}$ is $C_1$-$C_8$, preferably $C_1$-$C_6$, more preferably $C_4$ alkylene independently substituted with one or more $R_{22}$, wherein $R_{22}$ is as defined herein.

In some embodiments, the compound of Formula V has the structure of Formula VI following, wherein $R_{21}$ is substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

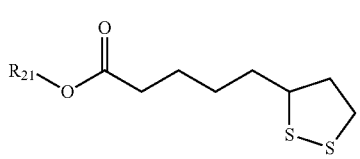
Formula VI

In some embodiments, $R_{21}$ is alkyl, preferably $C_1$-$C_6$ alkyl, more preferably $C_1$-$C_3$ alkyl, most preferably $C_1$, $C_2$, or $C_3$ alkyl, examples of which include, but are not limited to, the compounds set forth below:

TABLE 4

Active Agent Alkyl Esters

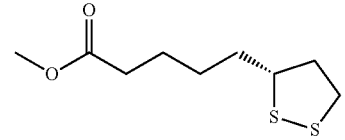

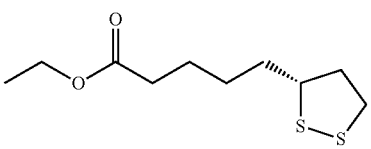

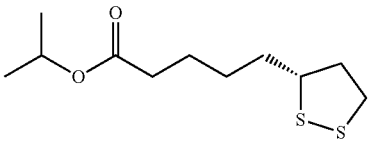

In some embodiments, $R_{21}$ is alkyl, preferably $C_1$-$C_6$ alkyl, more preferably $C_3$-$C_5$ alkyl, most preferably $C_3$, $C_4$ or $C_5$ alkyl, which in turn is multiply substituted with —OH. In some embodiments, $R_{21}$ is alkyl substituted with 1, 2, 3, 4 or even 5 hydroxyl functionalities. All diastereomeric, enantiomeric and regioisomeric forms of compounds of Formulae V, VI, VI(R), and VI(S) are contemplated herein.

Exemplary compounds according to any of Formulae V, VI, VI(R), and VI(S) include, but are not limited to, the compounds set forth below:

TABLE 5

Active Agent Substituted Alkyl Esters

[Chemical structures of six active agent substituted alkyl esters]

In some embodiments, $R_{21}$ is $R_{26}$-substituted or unsubstituted alkyl or $R_{26}$-substituted or unsubstituted heteroalkyl, and $R_{26}$ is independently —NH$_2$, =NH, —PO$_3$H$_2$, —OH, —CO$_2$H, $R_{27}$-substituted or unsubstituted alkyl, $R_{27}$-substituted or unsubstituted cycloalkyl, $R_{27}$-substituted or unsubstituted heteroalkyl, $R_{27}$-substituted or unsubstituted heterocycloalkyl, $R_{27}$-substituted or unsubstituted aryl, or $R_{27}$-substituted or unsubstituted heteroaryl.

In some embodiments, $R_{21}$ is $R_{26}$-substituted alkyl or $R_{26}$-substituted heteroalkyl, wherein $R_{26}$ is independently present in one or more occurrences, and in each occurrence is independently unsubstituted alkyl, preferably methyl. In some embodiments, $R_{21}$ is aminoalkyl, preferably aminoethyl, and $R_{26}$ is independently present at the pendant nitrogen 0, 1, 2 or even 3 times. In some embodiments, $R_{21}$ is a choline substituent in ester attachment with the lipoic acid structure set forth below. The structure may include a counterion, wherein the counterion is any pharmaceutically acceptable counterion capable of forming a salt with the choline lipoate:

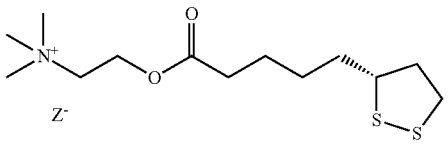 [SMILES: C[N+](C)(C)CCOC(=O)CCCC[C@@H]1CCSS1]

In some embodiments, a substituted group substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene or substituted heteroarylene within a compound described herein is substituted with at least one substituent group. In other embodiments, at least one or all of these groups are substituted with at least one size-limited substituent group. Alternatively, at least one or all of these groups are substituted with at least one lower substituent group.

C. Salts

The compounds described herein can also be provided as a pharmaceutically acceptable salt. The term "pharmaceutically acceptable salt" includes salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Examples of such salts include, but are limited to, hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In one embodiment, the counterion ion is the 1,3-dihydroxy-2-(hydroxymethyl)propan-2-aminium cation (i.e., a tromethamine salt):

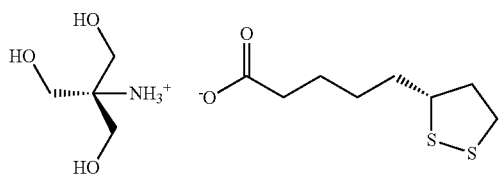

III. Methods of Use

The agents described herein can be employed in a method including the step of providing an active agent to a cell, either in vitro or in vivo.

The active agents described herein can be employed in a method for treating or preventing oxidation damage to cells. Such a method includes the step of administering a pharmaceutical composition comprising an active agent to a cell, either in vitro or in vivo.

As stated above, the agents can be delivered to cells in vitro or in vivo. In one embodiment, the cells are in vivo. In either case, the cells can be ocular cells, e.g., lens cells. In one embodiment, the agent is delivered to a lens, either in vitro or in vivo. Because oxidative damage has been implicated in other disorders including cancer, the agents may prove useful for administration to any type of cell exhibiting or prone to oxidative damage.

In one embodiment, the compounds described herein can be used in a method for treating ocular disease. Exemplary ocular diseases include, but are not limited to: presbyopia, cataract, macular degeneration (including age-related macular degeneration), retinopathies (including diabetic retinopathy), glaucoma, and ocular inflammations. In one embodiment, the ocular disease to be treated is cataract. In another embodiment, the ocular disease to be treated is treat presbyopia.

The methods preferably utilize a therapeutically effective amount of the active agent. The term "therapeutically effective amount" means an amount that is capable of preventing, reducing, reversing, and/or slowing the rate of oxidative damage. For ocular applications, a therapeutically effective amount may be determined by measuring clinical outcomes including, but not limited to, the elasticity, stiffness, viscosity, density, or opacity of a lens.

Lens elasticity decreases with age and is a primary diagnostic and causative factor for presbyopia. Lens elasticity can be measured as accommodative amplitude in diopters (D). FIG. 1 depicts the average elasticity in diopters of an untreated human lens as a function of age in years. The lower the value of D, the less elastic the lens. In one embodiment, the agents described herein can decrease and/or maintain D at a value that is greater than the D value exhibited by an untreated lens of about the same age. In other words, the agents can keep accommodative amplitude "above the line" depicted in FIG. 1 (the solid line is mean accommodative amplitude). In one embodiment, D is increased and/or maintained at a value about 2, 5, 7, 10, 15, 25, 50, 100, 150, or 200 percent above the line. However, as individual lenses may differ with respect to average values, another embodiment provides any increase in accommodative amplitude, maintenance of accommodative amplitude, or reduction in the rate of decline of accommodative amplitude (i.e., reduction in the rate of decrease in diopters) for an individual lens compared to the accommodative amplitude of the same lens before treatment. Accordingly, in another embodiment, the methods provide an increase in accommodative amplitude of about 0.25 to about 8 diopters, or at least about 0.1, 0.2, 0.25, 0.5, 1, 1.2, 1.5, 1.8, 2, 2.5, 3, 5, or 8 diopters compared to the same lens before treatment.

Figure 2:
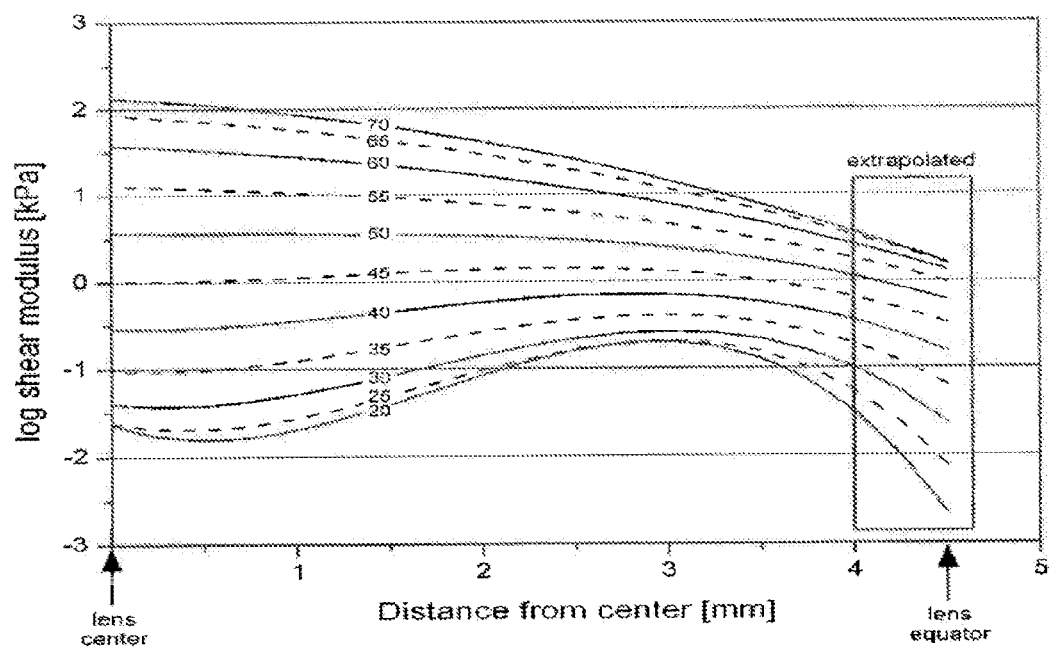
FIG. 2 shows a trend graph of the shear modulus versus position in the lens and age. Weeber, H A et al. 2007. Stiffness gradient in the crystalline lens. Graefes Arch Clin Exp Ophthalmol 245(9):1357-66. The line at the bottom is the 20-year-old lens; the line at the top is the 70-year-old lens. The modulus increases with age for all positions in the lens. Measurements were taken up to 4.0 mm from the lens centre. The lines are extrapolated to a radius of 4.5 mm (lens diameter 9.0 mm).

Lens elasticity can also be measured by the unit of elasticity E. The higher the value of E, the less elastic the lens. FIG. 2 depicts the average elasticity (E) of an untreated human lens as a function of age in years. In one embodiment, the agents described herein can decrease and/or maintain E at a value that is less than the E value exhibited by an untreated lens of about the same age. In other words, the agents can keep lens elasticity "below the line" depicted in FIG. 2. In one embodiment, E is decreased and/or maintained at a value about 2, 5, 7, 10, 15, 25, 50, 100, 150, or 200 percent below the line. However, as individual lenses may differ with respect to average values, another embodiment provides any increase in elasticity, maintenance of elasticity, or reduction in the rate of decline of elasticity (i.e., reduction in the rate of increase in E value) for an individual lens compared to the elasticity of the same lens before treatment.

Figure 3:
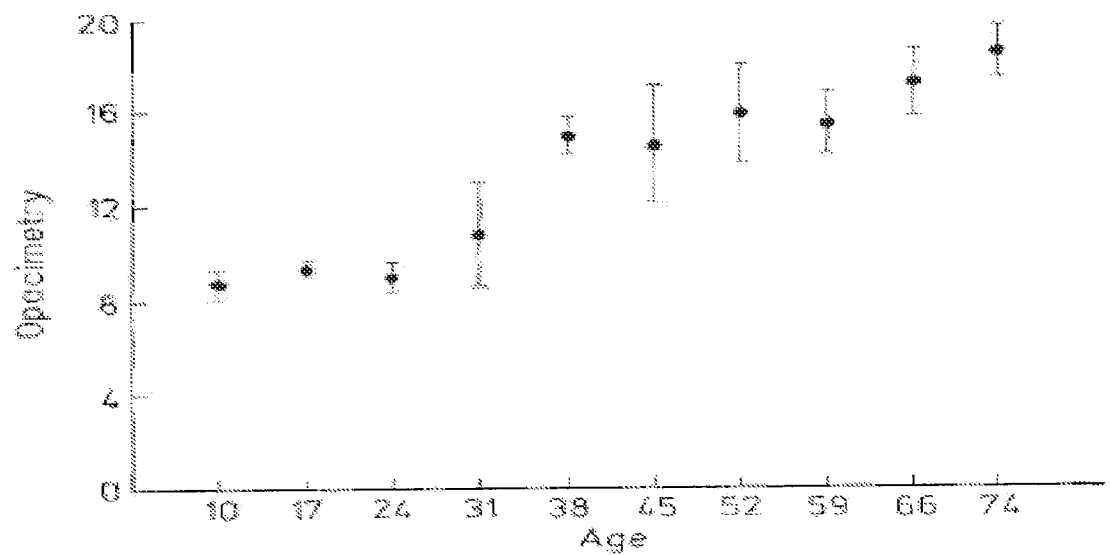
FIG. 3 depicts the average opacity (opacimetry) of an untreated human lens as a function of age in years. Bonomi, L et al. 1990. Evaluation of the 701 interzeag lens opacity meter. *Graefe's Arch Clin Exp Ophthalmol* 228(5):447-9. Lens opacity was measured in 73 healthy subjects between 10 and 76 years of age without slit-lamp evidence of cataract and with a visual acuity of 20/20. These subjects were classified into ten age groups. This study was carried out using the Interzeag Opacity Meter according to the procedure described by Flammer and Bebies (Flammer J, Bebie H. 1987. Lens Opacity Meter: a new instrument to quantify lens opacity. Ophthalmologica 195(2):69-72) and following the suggestions of the operating manual for the instrument.

Therapeutic efficacy can also be measured in terms of lens opacity. Lens opacity increases with age and is a primary diagnostic and causative factor for cataract. FIG. 3 depicts the average opacity of an untreated human lens as a function of age in years. In one embodiment, the agents described herein can decrease and/or maintain opacity at a value that is less than the opacity value exhibited by an untreated lens of about the same age. In other words, the agents can keep lens opacity "below the line" depicted in FIG. 3. In one embodiment, lens elasticity is decreased and/or maintained at a value about 2, 5, 7, 10, 15, 25, 50, 100, 150, or 200 percent below the line. However, as individual lenses may differ with respect to average values, another embodiment provides any decrease, maintenance, or reduction in the rate of increase of opacity for an individual lens compared to the opacity of the same lens before treatment.

Therapeutic efficacy can also be measured as a reduction in the rate of cell proliferation, particularly lens epithelial cell proliferation. Thus, in some embodiments, therapeutic efficacy can be measured by cytostatic effect.

The active agent can be administered as a racemate or as an enantiomer. For example, lipoic acid and its derivatives are preferably administered to include the R form; cystine and its derivatives are preferably administered to include the L form. Synthetic methods to yield a racemate may be less expensive than stereo-specific processes including isolation/purification steps. On the other hand, administering a single enantiomer can lower the therapeutically effective amount, thus decreasing toxicity effects.

The agents described herein are preferably reducing agents. For example, the agents can possess a redox potential $E_0'(V)$ of about −0.01 to about −1.0, about −0.1 to about −0.5, about −0.2 to about −0.4, or about −0.3. The agents described herein preferably exhibit an acceptable toxicity profile, e.g., a median lethal dose ($LD_{50}$) of at least 10 μM, at least 20 μM, at least 40 μM, or at least 1 mM. Toxicity can be assessed by any method known in the art such as, for example, viability of human umbilical vein endothelial cells (HUVEC, first passage) using the MultiTox-Fluor assay (Promega) or Live/Dead® assay (Invitrogen). Of course, agents selected as pharmaceutical agents for the treatment of presbyopia should exhibit both antioxidant efficacy (reducing power) as well as a desirable safety profile (low toxicity). Accordingly, in one embodiment, a screening method is provided whereby dithiol compounds or derivatives are tested for reducing power and/or toxicity. In another embodiment, a method includes screening dithiol compounds or dithiol derivatives for their ability to increase lens elasticity either in vitro or in vivo.

The agents described herein preferably exhibit favorable membrane permeability, specifically corneal permeability. Corneal penetration can be measured by methods known in the art, such as, for example, those disclosed in Kim et al. (2005) "Aqueous penetration and biological activity of moxifloxacin 0.5% ophthalmic solution and gatifloxacin 0.3% solution in cataract surgery patients" *Ophthalmology* 112 (11):1992-96. In one embodiment, the agent enters the lens epithelial cells using a naturally occurring transport mechanism. For example, lipoic acid and cystine enter lens cells via specific plasma membrane symporters and antiporters. By using lipoic acid, cystine, or derivatives thereof, one can utilize a naturally occurring transport mechanism to deliver the agents to the lens cells.

Some agents described herein exist naturally in the untreated eye. Lipoic acid and cystine, for example, occur naturally in eye tissue. In general, a therapeutically effective amount of the exogenously administered agent is often at least about 1 or 2 orders of magnitude larger than the natural level of the agent. In one embodiment, the lipoic acid or derivative thereof is administered in a dose amount of up to about 1 mM. In one embodiment, the dose amount of lipoic acid or a derivative thereof is about 1 $\mu$M up to 1 mM, preferably about 0.25 mM to about 0.75 mM, or about 0.5 mM. In another embodiment, the dose amount of lipoic acid or derivative thereof is no more than 0.5 mM, 250 $\mu$M, 100 $\mu$M, 50 $\mu$M, 20 $\mu$M, or 10 $\mu$M. In another embodiment, cystine or a derivative thereof is administered in a dose amount of about 1 $\mu$M to about 20 $\mu$M. In yet another embodiment, the dose amount of cystine or a derivative thereof is no more than 20 $\mu$M, the limit of cystine solubility in aqueous solution, or no more than 15 $\mu$M, 12 $\mu$M, 10 $\mu$M, 7 $\mu$M, or 5 $\mu$M. The dose amount will depend on the route of administration as well as the age and condition of the patient. Similarly, the frequency of dosing will depend on similar factors as can be determined by one of ordinary skill in the art.

Efficacy has been demonstrated in vitro for specific exemplary dosing. FIG. 2 shows that the inelasticity increases by a factor of nearly 20 during the critical period from age 40 to 55 years. From current data, a 10 $\mu$M dose can decrease the inelasticity over 95% within a millimeter volume element (voxel). Extrapolation of these results to a volume element in the human lens suggests that using this treatment dose on a 55 year old person with a 10 kPA lens starting modulus value (see FIG. 2) could be reduced after treatment to a value of about 0.5 kPA (which then corresponds to a value typically seen with a 40 yr old person). FIG. 1 permits a conversion of these modulus values to optical amplitude: accommodative amplitude is normally reduced to almost 0 above 55 years, while a person at 40-45 years still exhibits around 4-5 diopters of accommodation.

The methods include preventative methods that can be performed on patients of any age. The methods also include therapeutic methods that can be performed on patients of any age, particularly patients that are at least 20, 25, 30, 35, 40, 45, 50, 52, 55, 57, 60, 70, 75, or 80 years of age.

IV. Pharmaceutical Compositions

In another embodiment, a pharmaceutical composition includes an agent as described herein and a pharmaceutically acceptable carrier. A "pharmaceutically acceptable carrier," as used herein refers to pharmaceutical excipients, for example, pharmaceutically, physiologically, acceptable organic or inorganic carrier substances suitable for enteral or parenteral application that do not deleteriously react with the active agent. Suitable pharmaceutically acceptable carriers include water, salt solutions (such as Ringer's solution), alcohols, oils, gelatins, and carbohydrates such as lactose, amylose or starch, fatty acid esters, hydroxymethyl cellulose, and polyvinyl pyrrolidine. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention.

The pharmaceutical composition may also contain one or more excipients as is well known in the art of pharmaceutical formulary. In one embodiment, the pharmaceutical composition is formulated for ocular use. That is, the pharmaceutically acceptable carrier and/or other excipients are selected to be compatible with, and suitable for, ocular use. Such carriers and excipients are well known in the art. The excipients may also be selected and/or formulated to improve the solubility of the compound. For example, the pharmaceutical composition can include one or more of emulsifiers, buffers, salts, preservatives, lubricants, polymers, solvents, and other known excipients for ocular pharmaceutical formulations. In one embodiment, the pharmaceutical composition includes an emulsifier and a buffered carrier such as Polysorbate 80 in HBSS (Hank's Balanced Salt Solution).

In one aspect, there is provided a pharmaceutical composition which includes a compound or pharmaceutically acceptable salt thereof in combination (e.g., in formulation) with a pharmaceutically acceptable excipient.

The compounds described herein can be formulated to achieve any delivery system known in the art such as immediate or sustained release delivery; systemic, ocular, or localized delivery; topical or injection delivery; prodrug or caged delivery systems, e.g., coumarin cages (as described, for example, in co-pending application U.S. Ser. No. 12/267,260), and the like.

Liquid form preparations include solutions, suspensions, and emulsions, for example, water or water/propylene glycol solutions. Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethyl cellulose, and other well-known suspending agents. Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Some compounds may have limited solubility in water and therefore may require a surfactant or other appropriate co-solvent in the composition. Such co-solvents include: Polysorbate 20, 60, and 80; Pluronic F-68, F-84, and P-103;

cyclodextrin; and polyoxyl 35 castor oil. Such co-solvents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The compositions of the present invention may additionally include components to provide sustained release and/or comfort. Such components include high molecular weight, anionic mucomimetic polymers, gelling polysaccharides, and finely-divided drug carrier substrates, as known in the art.

The compounds can be administered to a lens by any route of administration including, but not limited to, topical, subtenons, subconjunctival, intracameral, intravitreal, or iontophoresis routes. In one embodiment, the agent can be delivered topically, e.g., via an eye drop, gel, ointment, or salve. In other embodiment, the compound can be delivered via an acute delivery system, e.g., using nanotubes, local injection, micro-injection, syringe or scleral deposition, or ultrasound.

Pharmaceutical compositions provided by the present invention include compositions wherein the active ingredient is contained in a therapeutically effective amount, i.e., in an amount effective to achieve its intended purpose. The actual amount effective for a particular application will depend, inter alia, on the condition being treated. For example, when administered in methods to treat cancer, such compositions will contain an amount of active ingredient effective to achieve the desired result (e.g. decreasing the number of cancer cells in a subject).

A. Dose Amounts

In one embodiment, the active agent is present in the pharmaceutical composition in an amount of about 0.1% to about 10% by weight, more specifically about 0.25% to about 10%, about 0.5% to about 10%, about 1% to about 8%, about 3% to about 7%, about 2% to about 5%, about 5% to about 7%, or about 5%. In another embodiment, the active agent is present in the pharmaceutical composition in an amount about 1 µM up to 1 mM, preferably about 0.25 mM to about 0.75 mM, or about 0.5 mM.

In some embodiments, a relatively low dose is called for. One such circumstance may be a preventative composition where the objective is to prevent rather than reverse oxidative damage. Another circumstance may be a priming or starting dose that would be titrated upward according to the subject's responsiveness and treatment objectives. In some embodiment, the active agent is present in an amount of about 0.1% to about 5%, about 0.1% to about 3%, about 0.1% to about 1%, about 1% to about 3%. In some embodiments, the active agent is present in an amount of less than about 250 µM, about 5 µM to about 250 µM, or about 10 µM to about 100 µM.

The dosage and frequency (single or multiple doses) of compound administered can vary depending upon a variety of factors, including route of administration; size, age, sex, health, body weight, body mass index, and diet of the recipient; nature and extent of symptoms of the disease being treated; presence of other diseases or other health-related problems; kind of concurrent treatment; and complications from any disease or treatment regimen. Other therapeutic regimens or agents can be used in conjunction with the methods and compounds of the invention.

Therapeutically effective amounts for use in humans may be determined from animal models. For example, a dose for humans can be formulated to achieve a concentration that has been found to be effective in animals. The dosage in humans can be adjusted by monitoring presbyopia in the human subject and adjusting the dosage upwards or downwards, as described above.

Dosages may be varied depending upon the requirements of the subject and the compound being employed. The dose administered to a subject, in the context of the present invention, should be sufficient to effect a beneficial therapeutic response in the subject over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the disease state of the subject.

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g. Fingl et al., In: THE PHARMACOLOGICAL BASIS OF THERAPEUTICS, Ch. 1, p. 1, 1975. The exact formulation, route of administration, and dosage can be chosen by the individual physician in view of the patient's condition and the particular method in which the compound is used.

B. Co-Administration of Additional Active Agents

The compounds described herein can be used in combination with one another, with other active agents known to be useful in ocular disease, or with adjunctive agents that may not be effective alone, but may contribute to the efficacy of the active agent. For example, adjunctive agents might include one or more amino acids or choline to enhance the efficacy of the active agent. The combinations can be advantageous, e.g., in reducing metabolic degradation.

The term "co-administer" means to administer more than one active agent, such that the duration of physiological effect of one active agent overlaps with the physiological effect of a second active agent. In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another.

Without being bound by theory, it is believed that the administration of an active agent, e.g., lipoic acid or a derivative thereof, and an adjunctive agent such as choline, can be particularly advantageous in a conjugated form. The conjugate compound be applied to the cornea, and penetration is achieved due to the bi-phasic (water and lipid soluble) nature of the conjugate compound. As the conjugate goes through the cornea, naturally present esterases (enzymes) separate lipoic acid from choline. The lipoic acid (now a pro-drug) in the aqueous bathes the lens and enters the lens epithelial cells (due to low molecular weight and size), and there is reduced by any one of several oxido-reductases (enzymes such as thioredoxin and thioltransferase) to form dihydrolipoic acid. Dihydrolipoic acid now has two extra hydrogen atoms to donate to a disulfide complex (e.g., protein disulfide PSSP), separating the two sulfur atoms into sulfhydryl molecules (e.g., protein cysteine residues PSH with free SH groups) thus breaking the inter-cytosol protein cross-links. Breaking these cross-link is what reduces the lens stiffness. Once donation of the hydrogen atoms to the sulfur atom, the dihydrolipoic acid becomes lipoic acid and is available for recycling in the cell to become dihydrolipoic acid or converted to a natural degraded by product thiolactone and excreted.

C. Co-Administration with a Biochemical Energy Source

In one embodiment, a reducing agent, such as one of the compounds described herein, is co-administered with a biochemical energy source. A biochemical energy source facilitates reduction by participating as an intermediate of energy metabolic pathways, particularly the glucose metabolic pathway. Exemplary intermediates of this pathway are depicted by, e.g., Zwingmann, C. et al. 2001. 13C Isotopomer Analysis of Glucose and Alanine Metabolism Reveals Cytosolic Pyruvate Compartmentation as Part of Energy Metabolism in Astrocytes. GLIA 34:200-212. Exemplary biochemical energy sources include, e.g., glucose or a portion thereof (e.g., glucose-6-phosphate (G6P)), pyruvate (e.g., ethyl pyruvate), NADPH, lactate or derivative thereof. G6P may be favored over glucose since a formulation including glucose may further benefit from the addition of preservatives. In one embodiment, the biochemical energy source is an intermediate in a cytosolic metabolic pathway. Exemplary cytosolic pathway intermediates include, e.g., glucose, pyruvate, lactate, alanine, glutamate, and 2-oxoglutarate. In another embodiment, the biochemical energy source is an intermediate in a mitochondrial metabolic pathway. Exemplary mitochondrial pathway intermediates include, e.g., pyruvate, TCA-cycle intermediates, 2-oxoglutarate, glutamate, and glutamine. In one embodiment, the biochemical energy source is pyruvate compound (e.g., ethyl pyruvate). In another embodiment, the biochemical energy source is alanine.

In one embodiment, the agent is co-administered with glucose-6-phosphate (G6P), NADPH, or glucose. In one embodiment, the agent is activated by an endogenous chemical energy, e.g., endogenous glucose. For example, endogenous glucose can activate lipoic acid or a derivative thereof to dihydrolipoic acid (DHLA) or a corresponding derivative thereof.

EXAMPLES

Example 1

In vitro Efficacy Studies

Increase in Elasticity: Pairs of mouse lenses were incubated in medium 200 supplemented with an antibiotic, an antimycotic, in the presence or absence of lipoic acid (concentrations ranging from 0.5 jµM to 500 µM) for 8-15 hours. Each lens was removed from medium, weighed, and photographed on a micrometer scale. A coverslip of known weight (0.17899±0.00200 g) was placed on the lens, and the lens was photographed again on the micrometer scale. The diameter of each lens with and without the coverslip was determined from the photographs. The change in lens diameter produced by the force (coverslip) was computed $\Delta D = (D_{withcoverslip} - D_{withoutcoverslip})$. The results (FIG. 4, ‡) indicate that lipoic acid at concentrations≥9.6 µM caused a statistically significant increase in $\Delta D$, $p<0.0001$.

Figure 4:
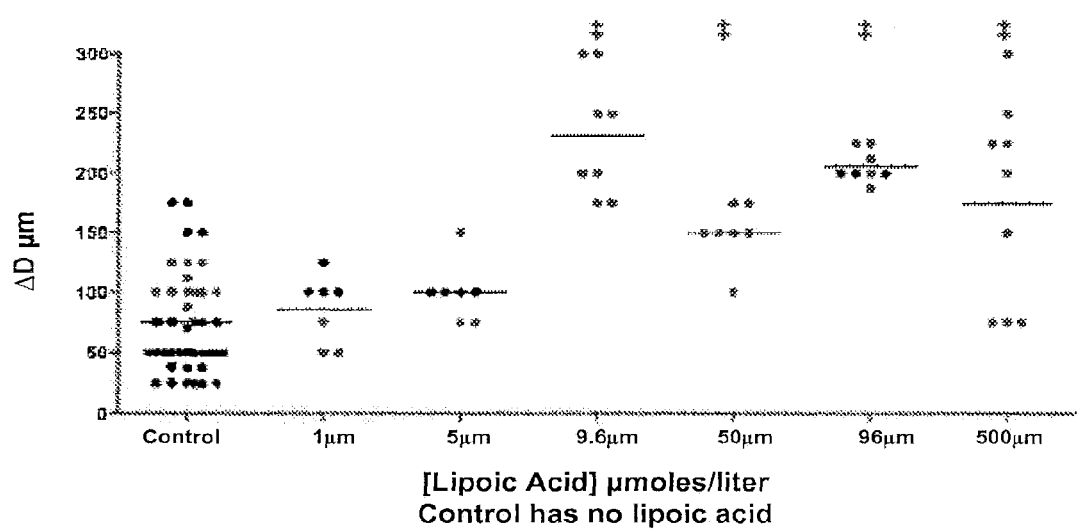
FIG. 4 depicts a scatter plot of the change in ΔD (micrometers) in the absence (control) and presence of lipoic acid in lens organ culture experiments. The symbol ‡ designates significantly larger changes in ΔD when compared to controls. Statistical values are highly significant at p<0.0001 by unpaired t-test and by Kruskal Wallis test, which compared medians of each data set. The relative change in Young's modulus (E) can be calculated as the cubic value derived from the ΔD of the control divided by the ΔD of the experimental or E fractional change=(ΔD con/ΔDexp)^3.
Figure 5:
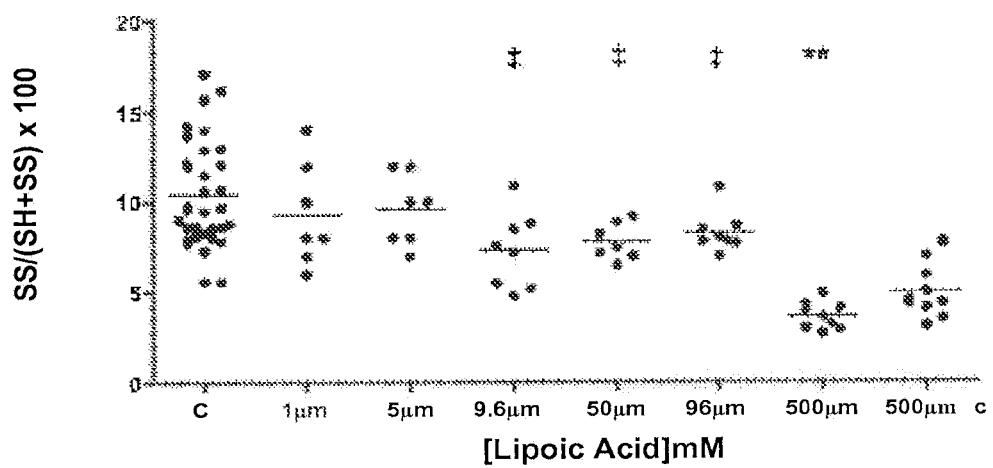
FIG. 5 depicts a scattergram of the percent of the total protein SH groups in disulfide bonds. Free SH groups were alkylated with 4-acetamido-4'-maleimidylstilbene-2,2'-sulfonic acid (c, 1 μM, 5 μM, 9.6 μM, 50 μM, 96 LM) or 7-diethylamino-3-(4'maleimidylphenyl)-4-methyl coumarin (500 μM, and 500 μM c). Following removal of the first alkylating agent, the S—S bonds were reduced and alkylated with fluorescein-5-maleimide. Absorption spectra were used to calculated total protein (A280 nm), free protein SH (A322 or A384), and protein SS (A490) using the appropriate extinction coefficients. The symbol ‡ indicates statistically significant difference of mean with mean of control (c, p≤0.05). The symbol ** indicates means of 500 μM lipoic acid and the 500 μM control were significantly different from each other (p=0.027).

Decrease in Disulfide Bonds: Lipoic acid at concentrations≥9.6 µM caused a statistically significant decrease in protein disulfides in the mouse lenses where there was a significant increase in $\Delta D$ (FIG. 4). Mouse lenses were homogenized in a denaturing buffer containing a fluorescent alkylating agent to modify the free SH groups. After removing the alkylating agent homogenates were reduced and alkylated with a different fluorescent alkylating agent. Absorption spectra of the modified proteins were used to calculate free protein SH and protein SS groups. The results are shown in FIG. 5.

Example 2

Synthesis of (R)-Lipoamide

NHS Ester of (R)-Lipoic Acid. The NHS ester of (R)-lipoic acid was synthesized as described in Scheme 1 following.

Scheme 1. Synthetic scheme for NHS-ester of (R)-lipoic acid.

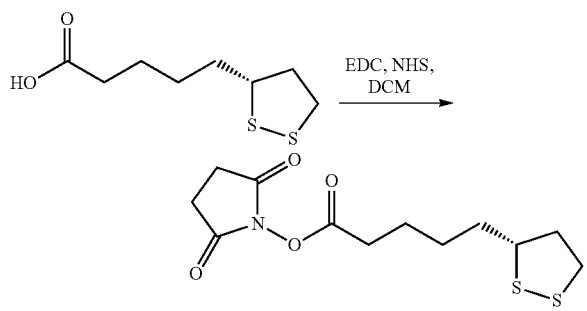

A solution of lipoic acid (25.6 g, 124 mmol), N-hydroxysuccinimide (15.6 g, 136 mmol), and EDC (26.1 g, 136 mmol) in anhydrous $CH_2Cl_2$ (300 mL) was stirred overnight at room temperature. The reaction mixture was diluted with ethyl acetate (500 mL) and washed with H2O (500 mL), saturated aqueous $NaHCO_3$ (500 mL), saturated aqueous NaCl (500 mL) and dried ($MgSO_4$). The drying agent was removed by filtration and the filtrate was concentrated to dryness giving the product as a yellow sold (35.4 g, 94%).

(R)-Lipoamide. (R)-lipoamide was synthesized as described in Scheme 2 following.

Scheme 2. Synthetic scheme for (R)-lipoamide.

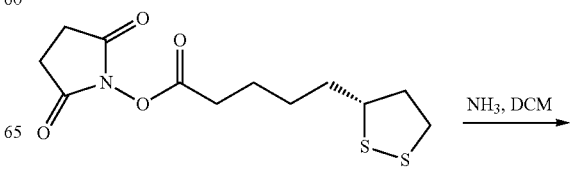

-continued

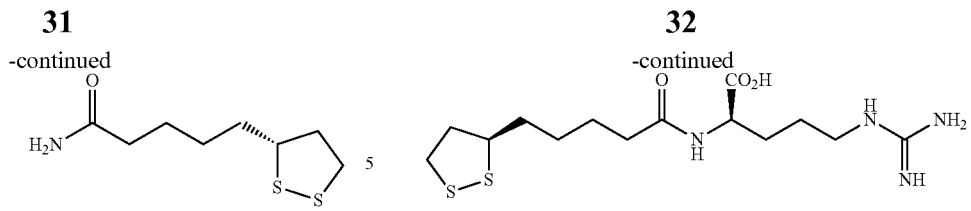

A solution of the NHS ester (2.7 g, 8.9 mmol) in anhydrous CH₂Cl₂ (50 mL) was cooled in a dry ice acetone bath. Ammonia was condensed into the reaction mixture over a period of 1-2 hours, then the reaction mixture was allowed to warm to room temperature overnight and diluted with CH₂Cl₂ (50 mL). Water (100 mL) was added and the mixture was stirred for 20 minutes. The phases were separated. The organic phase was washed with saturated aqueous NaCl (100 mL) and dried (Na₂SO₄). The drying agent was removed by filtration and the filtrate was concentrated to dryness giving the product as a yellow microcrystalline sold (1.56 g, 85%).

Example 3

Synthesis of an Arginine-Lipoic Acid Conjugate ("LA-Arg")

Pentafluorophenyl Ester of (R)-Lipoic Acid. The pentafluorophenyl ester of (R)-lipoic acid was synthesis as described in Scheme 3 following.

Scheme 3. Synthetic scheme for pentafluorophenyl ester of (R)-lipoic acid.

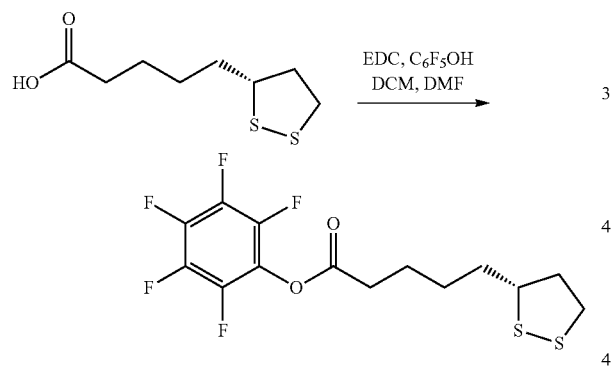

Solid EDC (1.04 g, 5.4 mmol) was added at once to a solution of lipoic acid (1.0 g, 4.8 mmol), and pentafluorophenol (1 g, 5.4 mmol) in anhydrous CH₂Cl₂:DMF (14 mL; (6:1)). The solution was stirred overnight at room temperature then concentrated to dryness. Flash column chromatography (SiO₂, 100% DCM) afforded the product as a clear, thick yellow oil (1.67 g, 94%).

LA-Arg. The arginine-lipoic acid conjugate was synthesis as described in Scheme 4 following.

Scheme 4. Synthetic scheme for LA-Arg.

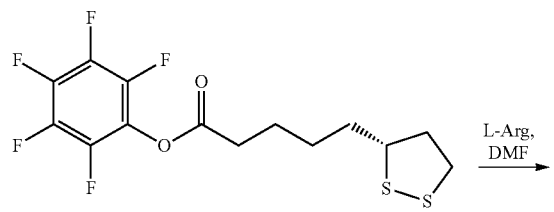

L-Arginine (530 mg, 3.1 mmol) was added at once to a solution of the Pfp ester (1.34 g, 3.6 mmol) in anhydrous DMF (4 mL). The reaction mixture was stirred at room temperature for 48 hours. Insolubles were isolated by vacuum filtration and the filter cake was washed with CHCl₃ (20 mL). The material was dried in vacuo overnight giving the product as a pale yellow solid (340 mg, 26%).

Example 4

Syntheses of Lipoic Acid Choline Ester

Lipoic acid choline ester was prepared according to the following synthetic route. Choline salts of alternative reducing agents can be similarly prepared by making the appropriate reagents substitutions. Also, one of ordinary skill in the art would recognize that these syntheses are provided as guidance and that reagents, conditions, amounts, temperatures, and the like may be modified without departing from the general synthetic pathway.

Step 1:

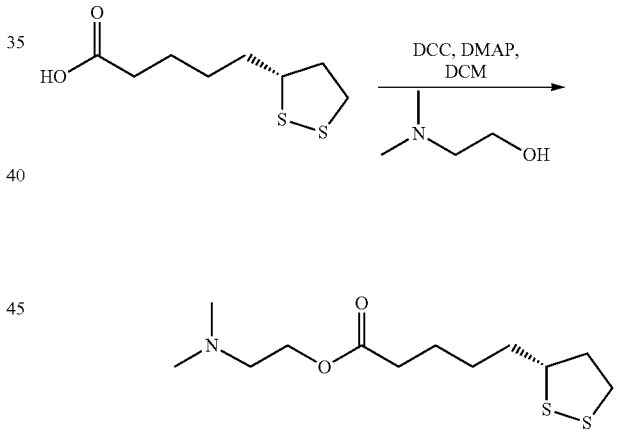

(R)-2-(dimethylamino)ethyl 5-(1,2-dithiolan-3-yl)pentanoate. A solution of DCC (11 g, 53 mmol) in anhydrous CH₂Cl₂ (20 mL) was added with stirring over 10-20 minutes to a cold (0° C.) solution of R-lipoic acid (10.0 g, 48.5 mmol), N,N-dimethylethanolamine (14.5 mL, 145 mmol, 3 eq.), and DMAP (600 mg, 4.9 mmol) in anhydrous CH₂Cl₂ (50 mL). Following complete addition, the cold bath was removed. After 18 hours at room temperature, all volatiles were removed under reduced pressure, and the resulting residue was purified by flash column chromatography (SiO₂, 2% MeOH in CH₂Cl₂) providing the desired product as a clear yellow oil (10.6 g, 79%). All data consistent with values reported in the literature. (See Courvoisier C. et al. 2006. Synthesis and effects of 3-methylthiopropanoyl thiolesters of lipoic acid, methional metabolite mimics. Bioorganic Chemistry 34(1):49-58.)

Step 2:

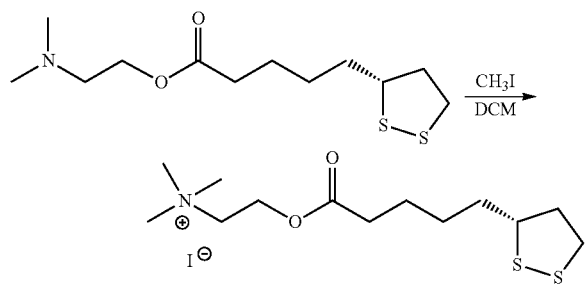

(R)-2-(5-(1,2-dithiolan-3-yl)pentanoyloxy)-N,N,N-(trimethyl)ethylammonium iodide. Methyl iodide (0.55 mL, 9.0 mmol) was added to a solution of the amine (2.5 g, 9.0 mmol) in anhydrous $CH_2Cl_2$ (20 mL). The reaction mixture was stirred overnight and slowly poured into diethyl ether (250 mL) with vigorous stirring. The choline salt was isolated by filtration as a free-flowing pale, yellow sold (3.7 g, 98%).

Example 4b

One-Step Synthetic Route

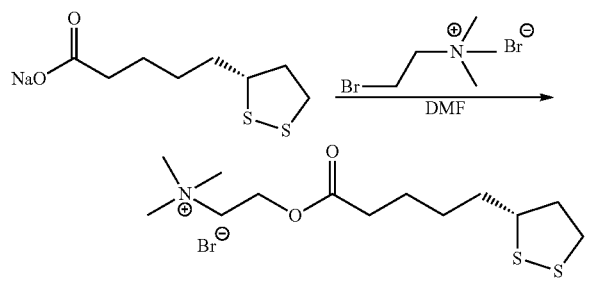

Example 5

Eye Drop Formulation of Lipoic Acid Choline Ester

The following eye drop formulation was prepared using lipoic acid choline ester as the active agent.

Formula A

| Ingredient | Concentration % by weight | Purpose |
|---|---|---|
| Lipoic acid choline ester | 5.0 | Active agent |
| Ethyl pyruvate | 0.1 | Energy source |
| Sodium phosphate monobasic monohydrate USP | 0.269 | Buffer |
| Sodium phosphate dibasic anhydrous USP | 0.433 | Buffer |
| Sodium chloride | 0.5 | Tonicity agent |
| Hydroxypropylmethylcellulose (HPMC), USP | 0.2 | Viscosity agent |
| De-ionized, pyrogen free water | to 100 mL | Solvent |

Formula B

| Ingredient | Concentration % by weight | Purpose |
|---|---|---|
| Lipoic acid choline ester | 5.0 | Active agent |
| Alanine | 0.5 | Stabilizer |
| Sodium phosphate monobasic monohydrate, USP | 0.269 | Buffer |
| Sodium phosphate dibasic anhydrous, USP | 0.433 | Buffer |
| Sodium chloride | 0.5 | Tonicity agent |
| Hydroxypropylmethylcellulose (HPMC), USP | 0.2 | Viscosity agent |
| De-ionized, pyrogen free water | to 100 mL | Solvent |

The eye drop formulation has a pH of 7.0.

The pharmaceutical formulation may be diluted to 100 ml filtered water (e.g., Millex syringe filter (0.45 micron 33 mm). The pharmaceutical composition may be packaged for multi-dose administration, e.g., 2-7 mL (e.g., 5 mL) eyedropper bottle with screw lid dropper.

The examples given above are merely illustrative and are not meant to be an exhaustive list of all possible embodiments, applications, or modifications of the invention. Thus, various modifications and variations of the described methods and systems of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes of carrying out the invention which are obvious to those skilled in the chemical arts or in the relevant fields are intended to be within the scope of the appended claims.

The disclosures of all references and publications cited above are expressly incorporated by reference in their entireties to the same extent as if each were incorporated by reference individually.

What is claimed is:

1. A method of treating presbyopia comprising administering to a subject a compound having a structure of Formula I-NC, or a pharmaceutically acceptable salt thereof:

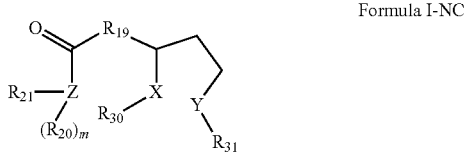

Formula I-NC wherein at least one of X and Y is sulfur, and the other is sulfur, selenium, or a sulfonic group;

$R_{19}$ is substituted or unsubstituted alkylene;

$R_{20}$, $R_{21}$, $R_{30}$, and $R_{31}$ are each independently hydrogen, substituted or unsubstituted alkyl, substituted or unsubstituted cycloalkyl, substituted or unsubstituted, heteroalkyl, substituted or unsubstituted heterocycloalkyl, substituted or unsubstituted aryl, or substituted or unsubstituted heteroaryl; wherein $R_{30}$ and $R_{31}$ may optionally be joined together or together form a single bond;

Z is N or O; and m is 0 or 1, wherein if Z is O, then m is 0, and if Z is N, then m is 1, and wherein the compound is not lipoic acid.

2. The method of claim 1, wherein one of X and Y is sulfur, and the other is sulfur or selenium.

3. The method of claim 1. wherein X and Y are both sulfur.

4. The method of claim 1. wherein $R_{19}$ is unsubstitutal alkylene.

5. The method of claim 4, wherein $R_{19}$ is $C_4$ alkylene.

6. The method of claim wherein the compound has a R configuration.

7. The method of claim 1, wherein the compound has a S configuration.

8. The method of claim 1, wherein the compound has a structure of Formula II-NC:

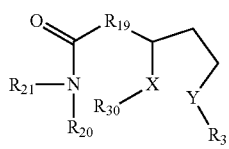

Formula II-NC wherein $R_{19}$, $R_{20}$, $R_{21}$, $R_{30}$, $R_{31}$, X and Y are as defined above.

9. The method of claim 1, wherein the compound has a structure of Formula V-NC:

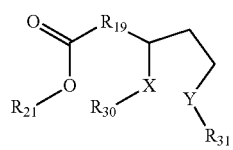

Formula V-NC wherein $R_{19}$, $R_{21}$, $R_{30}$, $R_{31}$, X and Y are as defined above.

10. The method of claim 9, wherein $R_{19}$ in Formula V-NC is unsubstituted alkylene.

11. The method of claim 10, wherein $R_{19}$ in Formula V-NC is $C_4$ alkylene.

12. The method of claim 11, wherein both X and Y in Formula V-NC are sulfur.

13. The method of claim 12, wherein $R_{30}$ and $R_{31}$ in Formula V-NC are each hydrogen.

14. The method of claim 13, wherein $R_{21}$ in Formula V-NC is $R_{26}$-substituted or unsubstituted alkyl, . . . , wherein $R_{26}$ is independently —$NH_2$, =NH, —$PO_3H_2$, —OH, —$CO_2H$, $R_{27}$-substituted or unsubstituted alkyl, . . . , wherein $R_{27}$ is independently —$N_2$, =NH, —$PO_3H_2$, —OH, —$CO_2H$, $R_{28}$-substituted or unsubstituted alkyl, $R_{28}$-substituted or unsubstituted cycloalkyl, $R_{28}$-substituted or unsubstituted heteroalkyl, $R_{28}$-substituted or unsubstituted heterocycloalkyl, $R_{28}$-substituted or unsubstituted aryl, or $R_{28}$-substituted or unsubstituted heteroaryl, wherein $R_{28}$ is independently unsubstituted alkyl, unsubstituted cycloalkyl, unsubstituted heteroalkyl, unsubstituted heterocycloalkyl, unsubstituted aryl or unsubstituted heteroaryl.

15. The method of claim 14, wherein $R_{21}$ in Formula V-NC is aminoalkyl.

16. The method of claim 15, wherein $R_{21}$ in Formula V-NC is aminoethyl.

17. The method of claim 16, wherein $R_{21}$ in Formula V-NC is N,N-dimethylaminoethyl.

18. The method of claim 16, wherein $R_{21}$ in Formula V-NC is N,N,N-trimethylaminoethyl.

19. The method of claim 1, further comprising administering a biochemical energy source.

20. A pharmaceutical composition comprising a compound having a structure of Formula V or Formula V-NC, or a pharmaceutically acceptable salt thereof:

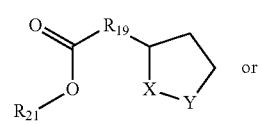

Formula V or

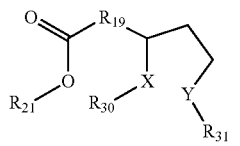

Formula V-NC wherein at least one of X and Y is sulfur, and the other is sulfur, selenium, or a sulfonic group;

$R_{19}$ is substituted or unsubstituted alkylene; $R_{30}$ and $R_{31}$ are each independently hydrogen, substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl; wherein $R_{30}$ and $R_{31}$ may optionally be joined together or together form a single bond; $R_{21}$ is a choline substituent;

and a pharmaceutically acceptable excipient.

21. A method of treating an ocular disease, comprising administering to a subject the pharmaceutical composition of claim 20.

22. The method of claim 21, wherein the ocular disease is presbyopia.

23. A pharmaceutical composition comprising a compound having a structure of Formula I or a pharmaceutically acceptable salt thereof:

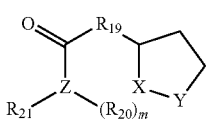

Formula I wherein both X and Y are sulfur;

$R_{19}$ is unsubstituted $C_4$ alkylene;

$R_{20}$ and $R_{21}$ are each independently hydrogen, substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl;

Z is N or O; and m is 0 or 1, wherein if Z is O then m is 0, and if Z is N, then m is 1, and wherein the compound is not lipoic acid; and a pharmaceutically acceptable excipient.

24. A method of treating an ocular disease, comprising administering to a subject the pharmaceutical composition of claim 23.

25. The method of claim 24, wherein the ocular disease is presbyopia.

26. A method of treating an ocular disease, comprising administering to a subject an active ingredient and choline.

27. The method of claim 26, wherein the active ingredient and choline are included in a single pharmaceutical composition.

28. The method of claim 26, wherein the active ingredient is lipoic acid.

29. The method of claim 28, wherein the choline and the lipoic acid are in a conjugated form.

30. The method of claim 27, wherein the ocular disease is presbyopia.

31. A method of treating an ocular disease, comprising administering to a subject an active ingredient of lipoic acid and an adjunctive agent.

32. The method of claim 31, wherein the lipoic acid and the adjunctive agent are included in a single pharmaceutical composition.

33. The method of claim 32. wherein the adjunctive agent is choline.

34. The method of claim 33, wherein the choline and the lipoic acid are in a conjugated form.

35. The method of claim 33, wherein the ocular disease is presbyopia.

\* \* \* \* \*